US009023027B2

(12) United States Patent  
Bar-Tal et al.

(10) Patent No.: US 9,023,027 B2  
(45) Date of Patent: May 5, 2015

(54) CURRENT LOCALIZATION TRACKER

(71) Applicant: Biosense Webster (Israel), Ltd., Yokneam (IL)

(72) Inventors: Meir Bar-Tal, Haifa (IL); Daniel Osadchy, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 190 days.

(21) Appl. No.: 13/756,729

(22) Filed: Feb. 1, 2013

(65) Prior Publication Data

US 2014/0221803 A1  Aug. 7, 2014

Related U.S. Application Data

(62) Division of application No. 12/556,639, filed on Sep. 10, 2009, now Pat. No. 8,456,182.

(60) Provisional application No. 61/101,308, filed on Sep. 30, 2008.

(51) Int. Cl.  
*A61B 18/04* (2006.01)  
*A61B 5/06* (2006.01)  
*A61B 18/14* (2006.01)  
(Continued)

(52) U.S. Cl.  
CPC .............. *A61B 5/063* (2013.01); *A61B 18/1492* (2013.01); *A61B 5/0533* (2013.01); *A61B 5/0538* (2013.01); *A61B 5/4836* (2013.01); *A61B 5/6852* (2013.01); *A61B 5/7217* (2013.01)

(58) Field of Classification Search  
CPC ............. A61B 18/1492; A61B 5/0533; A61B 5/0538; A61B 5/063; A61B 5/4836; A61B 5/6852; A61B 5/7217; A61B 2018/00755  
USPC .......................................................... 606/34  
See application file for complete search history.

(56) References Cited

U.S. PATENT DOCUMENTS 5,697,377 A   12/1997  Wittkampf  
5,713,946 A    2/1998  Ben-Haim  
(Continued)

FOREIGN PATENT DOCUMENTS

EP       1184684 A2     3/2002  
EP      1 743 575 B1    1/2007  
WO   WO 2008/108901 A8  9/2008

OTHER PUBLICATIONS

EP Search Report EP 11 15 7180 Dated Mar. 25, 2011.  
(Continued)

*Primary Examiner* — George Manuel  
(74) *Attorney, Agent, or Firm* — Louis J. Capezzuto

(57) ABSTRACT

A method includes positioning body-electrodes in galvanic contact with a body of a patient and positioning a mapping-tool, having a mapping-electrode, in a plurality of regions in the body. The method further includes tracking the mapping-tool at different positions in each of the regions using a location-measuring system, and for each region, generating a respective set of calibration-currents between the body-electrodes and the mapping-electrode at the different positions in the region. A respective relation is derived for each region between the respective set of the calibration-currents and the different positions, and is used in determining the location of an investigation-tool in response to the different respective relations and investigation-tool-currents.

16 Claims, 12 Drawing Sheets

(51) Int. Cl.
*A61B 5/053* (2006.01)
*A61B 5/00* (2006.01)

(56) References Cited

U.S. PATENT DOCUMENTS

| | | |
|---|---|---|
| 5,899,860 A | 5/1999 | Pfeiffer et al. |
| 5,983,126 A | 11/1999 | Wittkampf |
| 6,308,093 B1 | 10/2001 | Armoundas et al. |
| 6,574,498 B1 | 6/2003 | Gilboa |
| 2004/0030328 A1* | 2/2004 | Eggers et al. .......... 606/34 |
| 2005/0288586 A1 | 12/2005 | Ferek-Petric |
| 2007/0016007 A1 | 1/2007 | Govari et al. |
| 2007/0016028 A1 | 1/2007 | Donaldson et al. |
| 2007/0038078 A1 | 2/2007 | Osadchy |
| 2007/0060832 A1 | 3/2007 | Levin |
| 2009/0088630 A1 | 4/2009 | Moctezuma de la Barrera et al. |
| 2009/0088634 A1 | 4/2009 | Zhao et al. |
| 2009/0143670 A1 | 6/2009 | Daigneault |
| 2010/0079158 A1 | 4/2010 | Bar-Tal et al. |

OTHER PUBLICATIONS

Partial EP Search Report EP 09 25 2316 Dated Nov. 24, 2009.

* cited by examiner

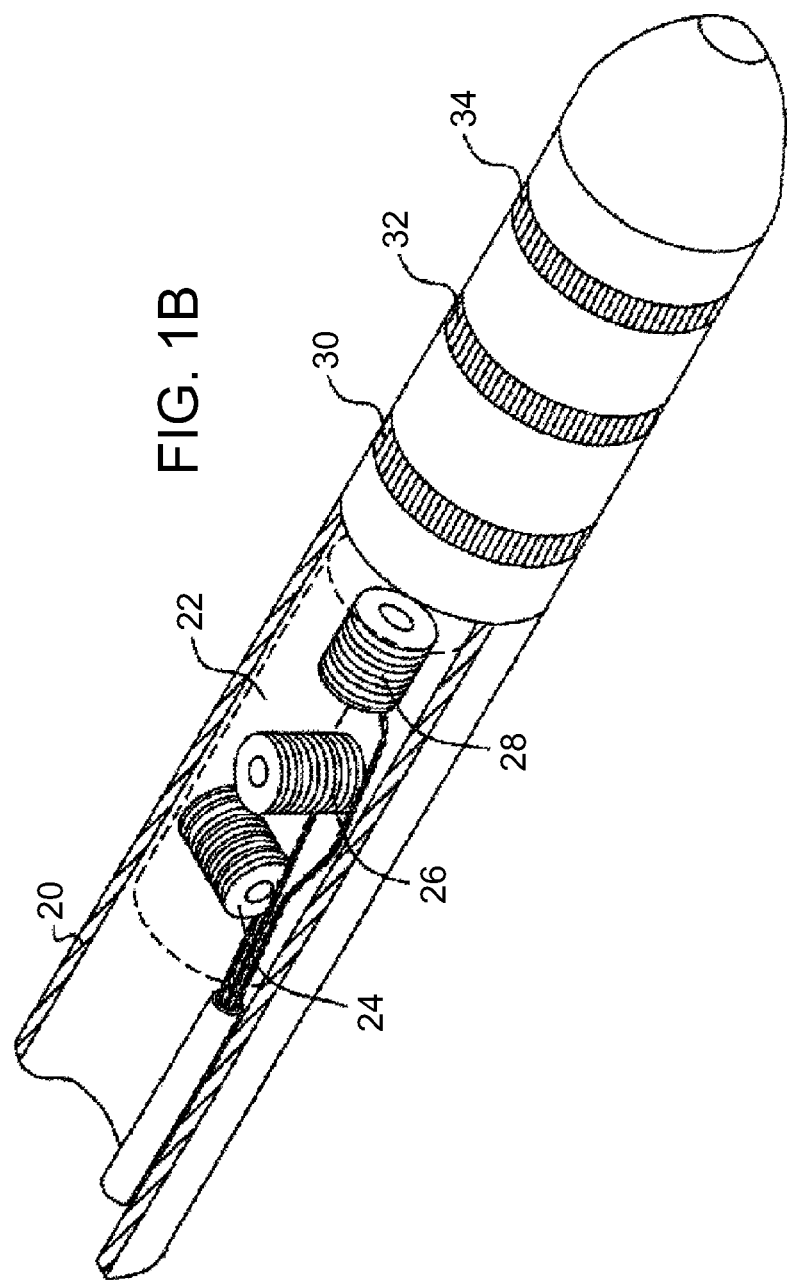

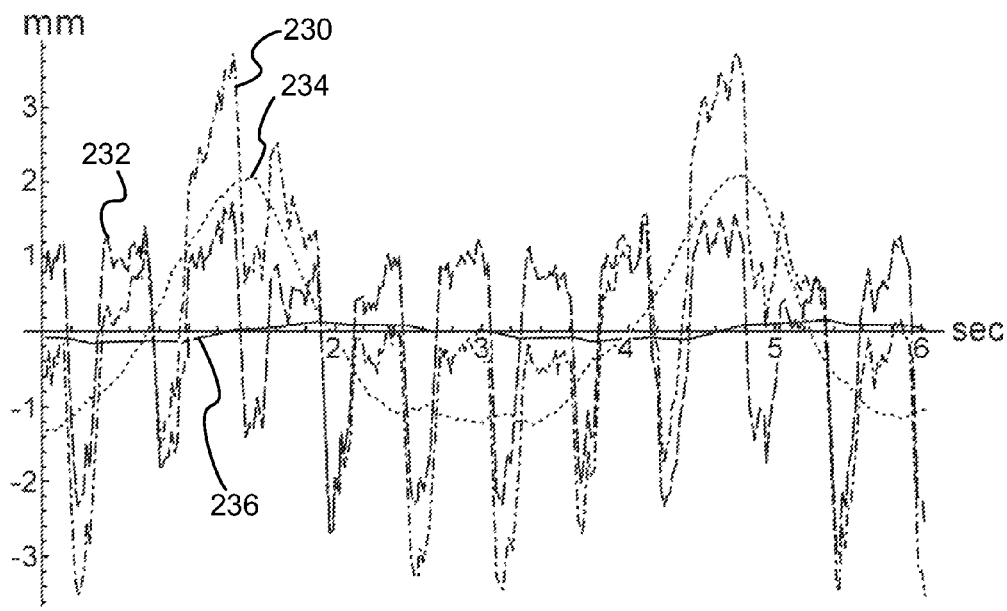
FIG. 6
FIG. 7
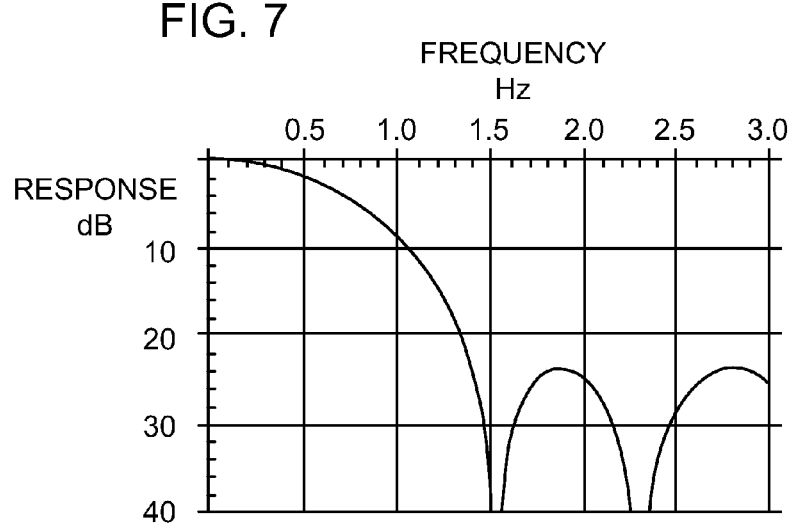

CURRENT LOCALIZATION TRACKER

CROSS-REFERENCE TO RELATED APPLICATION

This Application is a Divisional Patent Application of U.S. patent application Ser. No. 12/556,639 filed Sep. 10, 2009.

This application claims the benefit of U.S. Provisional Patent Application 61/101,308, filed Sep. 30, 2009, which is incorporated herein by reference.

FIELD OF THE INVENTION

The present invention relates generally to sensing the position of an object placed within a living body, and specifically to detection and compensation for artifacts experienced during position sensing of a probe in a living body.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

SUMMARY OF THE INVENTION

There is provided, according to an embodiment of the present invention, a method, including:

positioning body-electrodes in galvanic contact with a body of a patient;

positioning a mapping-tool, having a mapping-electrode, in a plurality of regions in the body of the patient;

tracking the mapping-tool at different positions in each of the regions using a location-measuring system;

for each region, generating a respective set of calibration-currents between the body-electrodes and the mapping-electrode at the different positions in the region;

deriving for each region a respective relation between the respective set of the calibration-currents and the different positions, such that the different ones of the regions have different respective relations;

positioning an investigation-tool having an investigation-electrode at a location in the body of the patient and generating investigation-tool-currents between the body-electrodes and the investigation-electrode at the location; and determining the location in response to the different respective relations and the investigation-tool-currents.

Typically, the body-electrodes include reference body-electrodes having reference electromagnetic (EM) sensors, the reference body-electrodes defining an EM coordinate system and a body coordinate system, the method including comparing calibration-currents of the reference body-electrodes with reference signals from the reference EM sensors so as to relate the EM coordinate system and the body coordinate system.

The method may include determining relative impedances between the body-electrodes to compensate for effective area changes between the body-electrodes and the body.

The method may include filtering the calibration-currents in response to at least one of respiration of the body and organ movement within the body so as to generate filtered calibration currents, wherein deriving the respective relation includes forming the relation in response to the filtered calibration currents.

In one embodiment, deriving the respective relation includes associating a volume including the different positions with the relation, and determining the location includes verifying that the location is within the volume. Typically, the respective relation includes a primary matrix, and the method includes dividing the volume into sub-volumes, and associating respective secondary matrices with the sub-volumes, each of the respective secondary matrices relating a respective subset of the different positions with a subset of the calibration-currents, and wherein determining the location includes selecting one of the secondary matrices in response to a given set of the calibration-currents. Usually, the location includes a weighted average of locations of the investigation-tool determined from the primary matrix and at least one of the secondary matrices.

Deriving the respective relation may include verifying that a number of the different positions exceeds a preset number of different positions prior to deriving the respective relation.

In an alternative embodiment, generating the respective set of calibration-currents includes determining if the set of calibration-currents corresponds with a subsequent set of calibration-currents by forming a comparison of different positions associated with the set and the subsequent set. The method may also include using the subsequent set in forming the relation if the comparison is invalid, and discarding the subsequent set if the comparison is valid.

In some embodiments, the investigation-tool is not tracked by the location-measuring system.

In a disclosed embodiment the method may also include:

positioning, simultaneously with the investigation-tool, a further investigation-tool having a further investigation-electrode at a further location in the body of the patient;

generating further investigation-tool currents between the body-electrodes and the further investigation-electrode; and determining the further location in response to the different respective relations and the further investigation-tool currents.

The location-measuring system may include at least one of an electromagnetic (EM) tracking system, a fluoroscopy tracking system, a magnetic resonance imaging (MRI) tracking system, and an ultrasound tracking system.

Typically, positioning the body-electrodes may include positioning at least one of the body-electrodes on the body of the patient. Alternatively, positioning the body-electrodes may include positioning at least one of the body-electrodes within the body of the patient.

Typically, the respective relation includes a matrix relating the respective set of calibration-currents and the different positions.

In a further disclosed embodiment, the method includes:

positioning a further-mapping-tool in contact with a moving organ of the body; and tracking the further-mapping-tool using the location-measuring system to generate further-mapping-tool positions;

wherein determining the location includes determining the location in response to the further-mapping-tool positions.

There is further provided, according to another embodiment of the present invention, apparatus for position tracking, including:

an investigation-tool having a conductive-electrode which is coupled to generate currents in a body of a patient in response to a driving voltage applied to the conductive-electrode:

an ablator body electrode, positioned in galvanic contact with the body, and configured to transfer ablation current to the body;

body surface electrodes, positioned in galvanic contact with the body, which receive respective body surface currents from the conductive-electrode; and a processor which determines a location of the investigation-tool in response to the respective body surface currents, while compensating for diversion of the respective body surface currents by the ablator body electrode.

Typically, compensating for the diversion includes recording the respective body surface currents prior to the transfer of the ablation current, and determining the location using the recorded respective body surface currents.

Alternatively, compensating for the diversion includes applying an ablator-body-electrode driving voltage to the ablator body electrode, and determining calibration currents in the body surface electrodes formed in response to the ablator-body-electrode driving voltage. The apparatus may include an ablator configured to generate the ablation current, wherein applying the ablator-body-electrode driving voltage to the ablator body electrode includes applying the ablator-body-electrode driving voltage via the ablator.

The apparatus may also include an ablator catheter, wherein applying the ablator-body-electrode driving voltage includes applying the ablator-body-electrode driving voltage while decoupling the ablator catheter from the ablator. Alternatively, applying the ablator-body-electrode driving voltage includes applying the ablator-body-electrode driving voltage while the ablator catheter is coupled to the ablator.

There is further provided, according to an embodiment of the present invention, a method for estimating impedance, including:

positioning body-electrodes in galvanic contact with a body of a patient;

positioning an investigation-tool having a conductive electrode in a plurality of regions within the body;

for each region, generating respective inter-electrode currents between the body-electrodes;

for each region, generating respective investigation-tool currents between the conductive electrode and the body-electrodes; and for each region, determining a respective impedance between each of the body-electrodes and the body in response to the respective inter-electrode currents and the respective investigation-tool currents.

Typically, generating the respective inter-electrode currents includes setting the inter-electrode currents to be respective alternating currents having different respective frequencies.

There is further provided, according to an embodiment of the present invention, apparatus, including:

body-electrodes positioned in galvanic contact with a body of a patient;

a mapping-tool, having a mapping-electrode, configured to be positioned in a plurality of regions in the body of the patient;

a location-measuring system configured to track the mapping-tool at different positions in each of the regions;

an investigation-tool, having an investigation-electrode, configured to be positioned at a location in the body of the patient and to generate investigation-tool-currents between the body-electrodes and the investigation-electrode at the location; and a processor, that for each region, generates a respective set of calibration-currents between the body-electrodes and the mapping-electrode at the different positions in the region, and derives for each region a respective relation between the respective set of the calibration-currents and the different positions, such that the different ones of the regions have different respective relations, and wherein the processor is configured to determine the location in response to the different respective relations and the investigation-tool-currents.

There is further provided, according to an embodiment of the present invention, a method for position tracking, including:

coupling an investigation-tool having a conductive-electrode to generate currents in a body of a patient in response to a driving voltage applied to the conductive-electrode:

positioning an ablator body electrode in galvanic contact with the body so as to transfer ablation current to the body;

positioning body surface electrodes in galvanic contact with the body so to receive respective body surface currents from the conductive-electrode; and determining a location of the investigation-tool in response to the respective body surface currents, while compensating for diversion of the respective body surface currents by the ablator body electrode.

There is further provided, according to an embodiment of the present invention, apparatus for estimating impedance, including:

body-electrodes positioned in galvanic contact with a body of a patient;

an investigation-tool having a conductive electrode, configured to be positioned in a plurality of regions within the body; and a processor, which for each region is configured to:

generate respective inter-electrode currents between the body-electrodes, generate respective investigation-tool currents between the conductive electrode and the body-electrodes, and determine a respective impedance between each of the body-electrodes and the body in response to the respective inter-electrode currents and the respective investigation-tool currents.

The present disclosure will be more fully understood from the following detailed description of the embodiments thereof, taken together with the drawings, in which:

BRIEF DESCRIPTION OF THE DRAWINGS

FIG. 1B is a schematic detailed view showing the distal end of the hybrid catheter, according to an embodiment of the present invention;

FIG. 6 is a graph of different components of the location of a coronary sinus reference catheter, according to an embodiment of the present invention;

FIG. 7 is a graph of a frequency response of a filter, according to an embodiment of the present invention;

DETAILED DESCRIPTION OF EMBODIMENTS

Overview

Figure 1A:
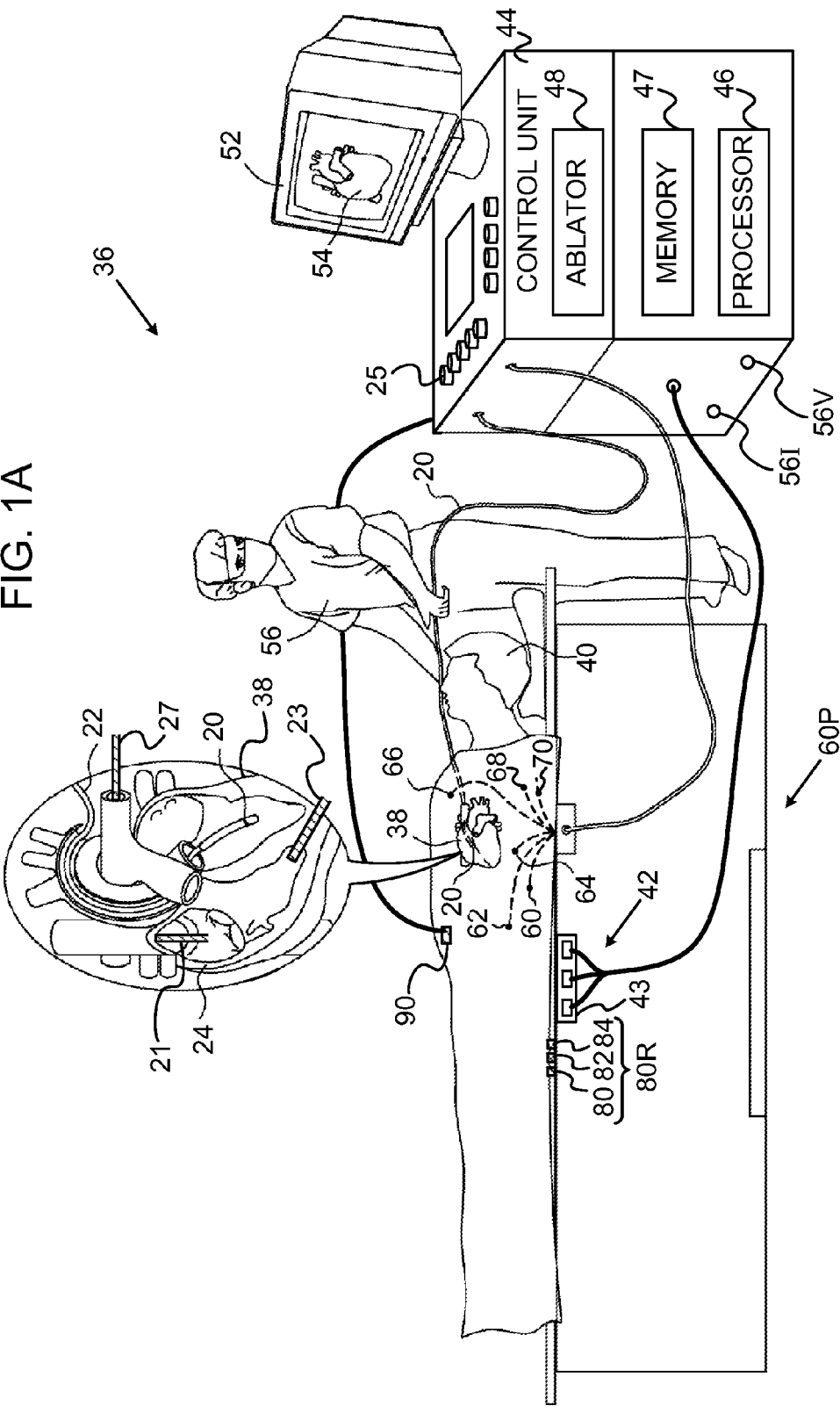
FIG. 1A is a schematic, pictorial illustration of a position sensing system, utilizing a hybrid catheter.

In embodiments of the present invention, two types of tracking sub-system are used for measuring the location and orientation of an object, herein by way of example assumed to be a catheter tip, within the body of a patient.

One of the sub-systems, herein termed an advanced current localization (ACL) tracker sub-system, generates a current from an electrode on the catheter tip and measures the current distribution at a number of patches placed on the body surface, and/or at conducting elements positioned within the body. The location of the electrode is calculated from the current distribution.

The second sub-system may be any tracking system that operates on a different principle to that of the ACL sub-system. The second sub-system typically provides more accurate results than those provided by the ACL sub-system when the latter operates alone. Second sub-systems that may be used include, but are not limited to, imaging systems such as electromagnetic (EM) systems, fluoroscopy systems, magnetic resonance imaging (MRI) systems, and ultrasound systems. The second sub-system may also comprise combinations of tracking systems operating on different principles to that of the ACL sub-system. Relations are formed between the results of the two sub-systems, and the relations are applied to the measured currents of the ACL sub-system in order to enhance its tracking accuracy. By way of example, in the description herein, the relations are assumed to be based on matrices.

In a disclosed embodiment described hereinbelow the second sub-system comprises an EM tracker sub-system. The EM tracker uses magnetic fields generated by three tri-coil sources in a location pad (LP) external to the body, and field measurements made by EM sensors located in the catheter tip, to calculate the catheter tip location. The EM tracker typically provides the catheter tip location and orientation with an accuracy of approximately 1 mm and 1 degree, respectively.

In a calibration phase of the disclosed embodiment, a mapping-tool having EM sensors and an electrode is moved to multiple positions within the body of the patient. The mapping-tool is also herein termed a hybrid catheter. EM measurements and current measurements are recorded for the multiple positions. The EM measurements are used to train the ACL tracker to determine, from the current measurements, a location with a higher degree of accuracy than that determined by the ACL tracker alone. The ACL tracker, after training, may be used in a tracking phase to track locations of investigation-tools, such as catheters, that do not have EM sensors.

Typically, many such investigation tools, also herein termed non-hybrid catheters, may be tracked simultaneously by applying alternating driving voltages having respective different frequencies to the different non-hybrid catheters.

The EM tracker location measurements are provided in LP coordinates, while ACL coordinates are provided in relation to body coordinates. In order to correlate the two location systems, two correlation techniques are used:

(1) The EM tracker locations are transformed to corresponding locations within a body coordinate system, which is defined by three patches on the patient's back.

(2) An internal reference catheter may be used to detect dynamic movement, which is typically mainly related to respiration.

In an alternative embodiment of the present invention, an ablator is used on the patient. The ablator uses an ablator body electrode, placed in contact with the body, which transfers ablation current from the ablator to the body. The ablator body electrode diverts current from the body surface electrodes, and the current diversion, if not compensated for, would cause errors in the positions determined by the processor. In a calibration process, the processor compensates for the current diversion, typically by applying a driving voltage to the ablator body electrode, so generating calibration currents in the body surface electrodes. The processor uses the calibration currents, and measurements of the current diverted through the ablator, to correct the errors in calculated catheter positions that would otherwise occur.

Some aspects of EM-ACL tracking are described in US Patent Application 2007/0016007, which is assigned to the assignee of the present application and the disclosure of which is incorporated herein by reference. Embodiments of the present invention improve the accuracy of EM-ACL tracking systems.

System Description

FIG. 1A is a schematic, pictorial illustration of a position sensing system 36, utilizing a hybrid catheter 20, and FIG. 1B is a schematic detailed view showing the distal end of the hybrid catheter, according to an embodiment of the present invention. The hybrid catheter may also be referred to herein as a mapping-catheter. A medical professional 56 is assumed to operate system 36.

By way of example, except where otherwise stated in the description hereinbelow, mapping-catheter 20 is assumed to be used in an invasive procedure within a chamber of a heart 38 of a subject 40. Alternatively, position sensing system 36 may be used with probes similar to catheter 20 in other body cavities. Subject 40 is placed in a magnetic field generated, for example, by positioning under the subject a location pad 43 containing magnetic field generator coils 42. The magnetic fields generated by coils 42 generate electrical signals in coils 24, 26 and 28 of an electromagnetic (EM) sensor 22 located at the distal end of catheter 20. The electrical signals are conveyed to a control unit 44, which analyzes the signals so as to determine the coordinates of the position and of the orientation of catheter 20. Alternatively, the coils in magnetic field sensor 22 may be driven to generate magnetic fields, which are detected by coils 42.

Control unit 44 includes a processor 46, typically a computer with appropriate signal processing circuits. The processor uses a memory 47, which typically comprises both volatile and non-volatile data storage devices, wherein data for operating system 36 is stored. The processor is coupled to drive a console 52, which may provide a visual display 54 of the location of catheter 20.

Control unit 44 comprises alternating current drivers 56I which processor 46 uses to supply currents to mapping-catheter-conductive-electrodes 30, 32, and 34 that are located at the distal end of mapping-catheter 20. Processor 46 sets the alternating frequency of the current supplied to each electrode of catheter 20 to be different. The catheter electrodes are connected by wires through the insertion tube of the catheter to current and voltage measurement circuitry in control unit 44.

The control unit is connected by wires to body surface electrodes, also referred to herein as body-electrodes, which may be any type of body electrodes known in the art, such as button electrodes, needle electrodes, subcutaneous probes, or patch electrodes. The body-electrodes are typically in galvanic contact with the body surface of subject 40, and receive body surface currents therefrom. Where the following description refers to patch electrodes or patches, it will be understood that embodiments of the present invention may use any of the other type of electrodes described above.

In some embodiments, one or more of the body-electrodes may be positioned in galvanic contact with, and inside, the body of subject 40. Typically, control unit 44 tracks the position of these internally located body-electrodes, for example by these body-electrodes being configured to have tracking coils similar to coils 24, 26 and 28 in catheter 20. Except where otherwise stated, the following description assumes, for simplicity, that the body-electrodes are located on the body of subject 40. Those having ordinary skill in the art will be able to adapt the description, mutatis mutandis, to cover body-electrodes positioned inside the body of subject 40.

By way of example, body surface electrodes are herein assumed to comprise adhesive skin patches 60, 62, 64, 66, 68 and 70, generically referred to herein as active current location (ACL) patches 60P, or by an ACL patch index "i," where i is an integer between 1 and 6. ACL patches 60P may be placed at any convenient locations on the body surface of subject 40 in the vicinity of the probe. ACL patches 60P typically have respective associated tracking coils, similar to coils 24, 26 and 28 in catheter 20. In alternative embodiments of the invention, the body surface electrodes may vary in number. The body surface electrodes receive differing mapping-currents from the electrodes of the mapping-catheter, and the differing currents are analyzed to determine a location or position of catheter 20. Catheter thus comprises two components for measuring its location, one component operating in an EM sub-system of system 36, the other component operating in an ACL sub-system of the system 36. Catheter 20 is also termed a hybrid catheter.

Control unit 44 also comprises voltage generators 56V, which are connected to ACL patches "i" by their connecting wires, and which processor 46 uses to measure the impedance of the ACL patches.

The currents from drivers 56I and generators 56V are differentiated by processor 46 operating the currents and voltages at different frequencies. Thus there are six unique frequencies for the generators supplying voltage to the ACL patches, and a multiplicity of other unique frequencies for the drivers supplying current to the catheters.

In system 36 there may be one or more other hybrid catheters, generally similar to catheter 20, which are tracked by the system generally as catheter 20 is tracked. For clarity, in FIG. 1A the other catheters are not shown. In addition, in system 36 there may be other non-hybrid catheters comprising one or more electrodes, similar to electrodes 30, 32, and 34, but not comprising a sensor such as sensor 22. Non-hybrid catheters are herein also referred to as investigation-catheters, and the electrodes of the investigation-catheters are also referred to as investigation-catheter-conductive electrodes. System 36 is able to track these investigation-catheters. By way of example, one such non-hybrid catheter 21 is shown in FIG. 1A.

In one embodiment there are approximately 90 frequencies for current drivers 56I, so that up to 90 catheter electrodes may be tracked simultaneously in system 36.

In system 36 a catheter 23, which may be a hybrid or a non-hybrid catheter, is assumed to be used to ablate a region in body 40. Catheter 23 is also referred to herein as the ablation catheter. To complete return of the ablation current used by ablation catheter 23, an ablator body electrode 90, herein also termed an ablation patch 90, is galvanically attached to body 40. Patch 90 and ablation catheter 23 are attached by wires to a radio-frequency (RF) ablator module 48 in console 40. The console also includes a switch 25 allowing professional 56 to operate module 48.

Skin patches, herein assumed by way of example to comprise three adhesive skin patches 80, 82, and 84, are typically placed on the back of subject 40 for use as position references. Patches 80, 82, and 84 are herein referred to generically as reference patches 80R. Each reference patch 80R has an EM sensor, which is generally similar to sensor 22, and which provides the position of its respective patch to processor 46. Reference patches 80R are connected to control unit 44 by wires.

System 36 may also include a reference position sensor, such as an internally-placed catheter, inserted into a moving organ of body 40, herein assumed to be heart 38, and maintained in a substantially fixed position relative to the moving organ. Herein the reference sensor is assumed to comprise a coronary sinus reference catheter (CSRC) 27, and is also referred to herein as reference catheter 27. Catheter 27 is typically a hybrid catheter. By comparing the position of catheter 20 to that of reference catheter 27, the coordinates of catheter 20 are accurately determined relative to the heart, irrespective of heart motion.

Typically, system 36 includes other elements, which are not shown in the figures for the sake of simplicity, and which are referred to as necessary in the following description. For example, system 36 may include an ECG monitor, coupled to receive signals from one or more body surface electrodes, so as to provide an ECG synchronization signal to control unit 44.

The configuration of FIG. 1A is an example configuration, which is chosen purely for the sake of conceptual clarity. In alternative embodiments, any other suitable configuration can also be used. Typically, processor 46 comprises a general-purpose processor, which is programmed in software to carry out the functions described herein. The software may be downloaded to the processor in electronic form, over a network, for example, or it may, alternatively or additionally, be provided and/or stored on tangible media, such as magnetic, optical, or electronic memory.

Figure 2A:
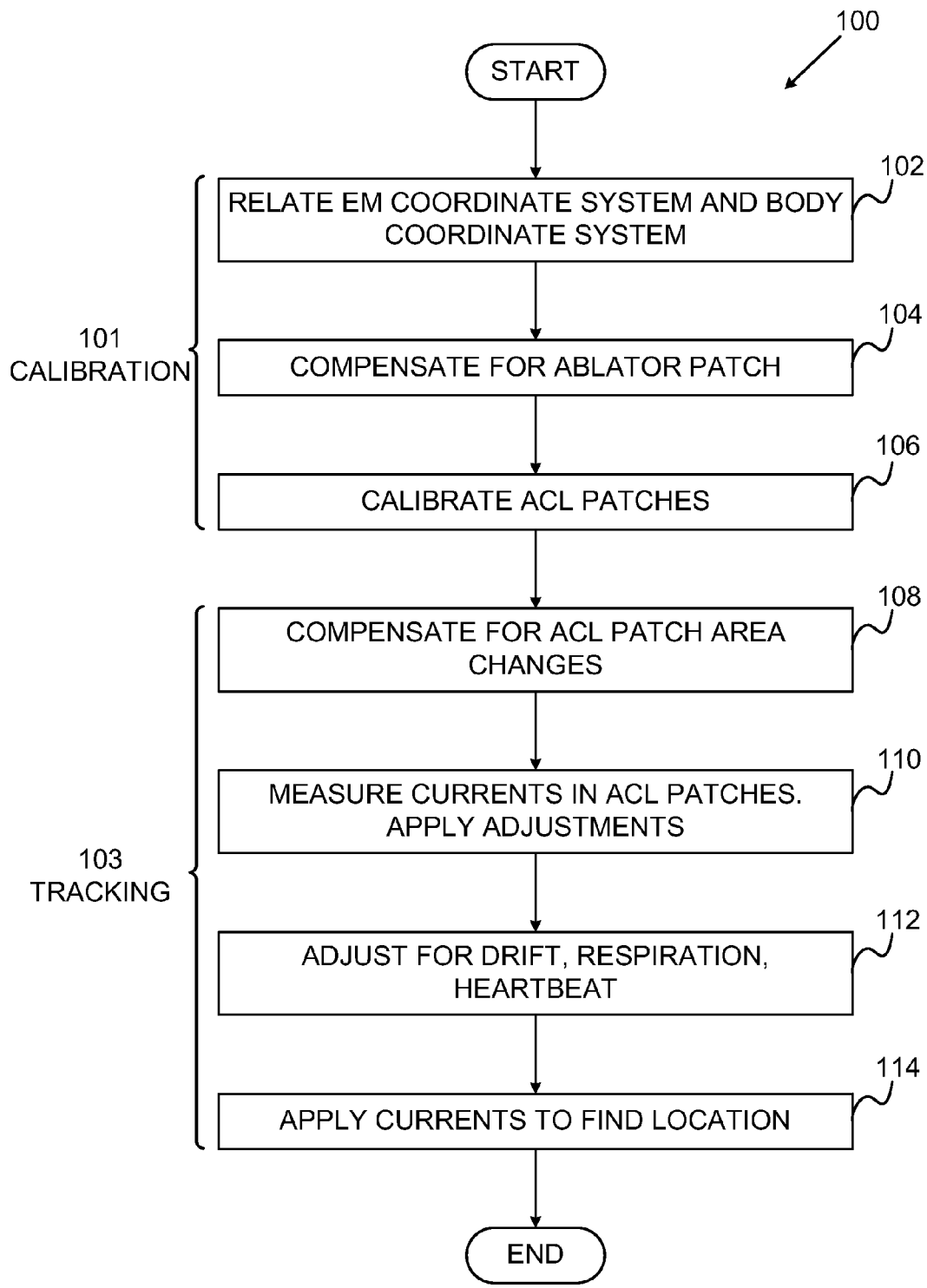
FIG. 2A is a flow chart schematically illustrating a process for operating the position sensing system.
Figure 2B:
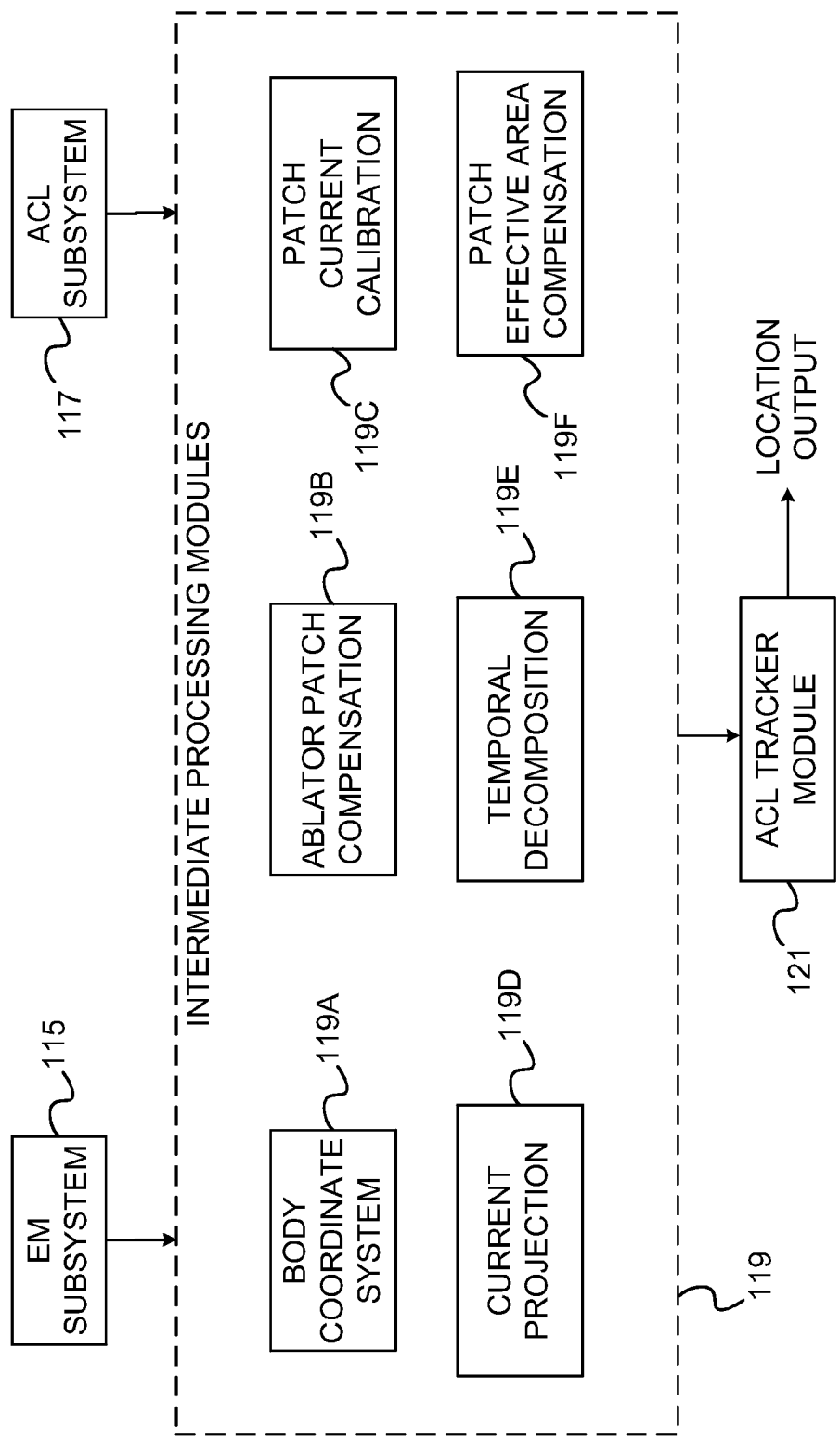
FIG. 2B is a simplified block diagram of the system, according to an embodiment of the present invention.

FIG. 2A is a flow chart 100 schematically illustrating a process for operating system 36, and FIG. 2B is a simplified block diagram of the system, according to an embodiment of the present invention. To operate system 36, professional 56, or another operator of the system, first operates the system in a calibration phase 101, after which the system is operated in a tracking phase 103. Actions performed in each of the steps of the two phases are described in detail below. As is also described below, some of the actions may be performed in either phase.

In a reference frame correlation step 102, coordinates measured in an EM reference frame and in an active current location (ACL) reference frame are correlated. An EM tracker sub-system 115 generates measurements in the EM reference frame; an ACL tracker sub-system 117 generates measurements in the ACL frame, also herein termed the Body Coordinate System. The EM tracker sub-system measures locations using the electromagnetic fields generated by coils 24, 26, and 28. The ACL tracker measures locations using currents through ACL patches 60P.

Except where otherwise indicated, the following steps of the flowchart are performed in intermediate processing modules 119, which comprise body coordinate system module 119A, ablator patch compensation module 119B, patch current calibration module 119C, current projection module 119D, temporal decomposition module 119E, and patch effective area compensation module 119F.

In an ablator patch compensation step 104, processor performs measurements to determine how measured currents through the ACL patches may be compensated for because of current diversion through the ablator patch. Processor 46 performs the measurements by generating currents in the ablator patch and/or the ACL patches.

In an ACL patch calibration step 106, processor 46, using similar currents to those used for step 104, determines differences in individual ACL patch impedances. The differences in the impedances affect the currents in the ACL patches that are measured by the processor.

In a patch compensation step 108 processor 46 compensates for changes in the ACL patches effective area. The changes are typically caused by factors such as change of conductivity of the patch, usually because of sweating, and partial peeling of the patch from the skin of the patient. Processor 46 uses currents similar to those generated in steps 104 and 106 to determine compensation factors.

In a current projection step 110, the processor measures the currents in the ACL patches that are generated by currents injected into catheters being tracked, and applies the adjustments determined in steps 104, 106, and 108 to the currents.

In a temporal adjustment step 112, the processor compensates for changes in the currents caused by three temporal factors: drift, respiration, and heartbeat. The compensation is implemented by applying different filters to the currents measured in step 110.

A final ACL step 114 comprises an initial training phase, wherein the processor stores current data and location data from the above steps and generates matrices relating the current and location data. ACL step 114 is performed in ACL tracker module 121. Once sufficient data has been obtained, processor 46 applies the generated matrices to the current data from step 112, to calculate the location for electrodes on catheter 20. The processor generates respective matrices for different "clusters," or regions, of the heart to improve the accuracy of current location.

The following description explains each of the steps of flowchart 100 in detail.

Body Coordinate System

Figure 3:
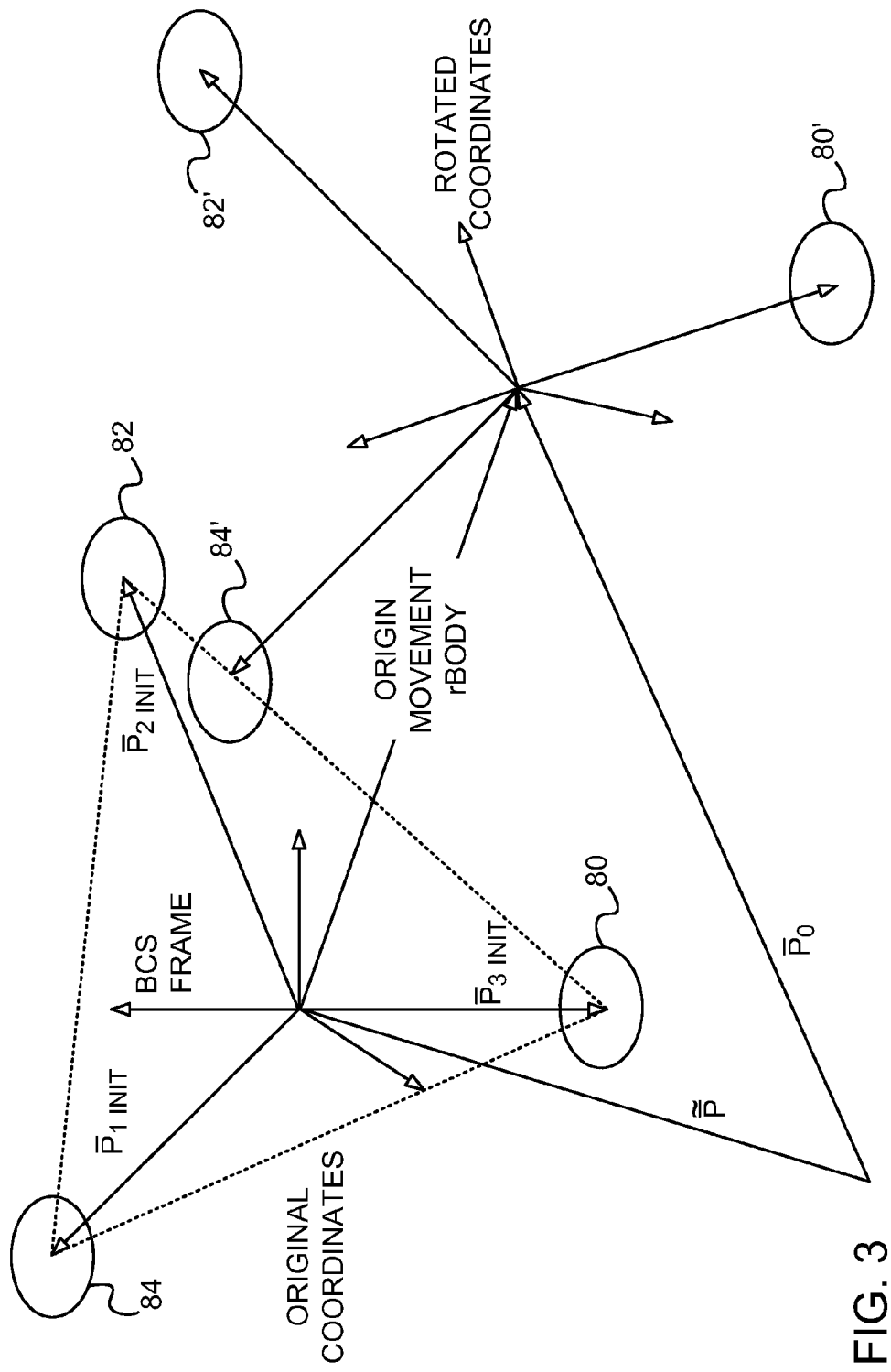
FIG. 3 is a schematic diagram illustrating a vector relationship for reference patches used in the position sensing system, according to an embodiment of the present invention.

FIG. 3 is a schematic diagram illustrating a vector relationship for reference patches 80R, according to an embodiment of the present invention. Initial positions of the patches are shown as patches 80, 82, and 84. Positions after movement are shown as patches 80', 82', and 84'.

In body coordinate system module 119A, processor 46 applies the relationship in performing reference frame correlation step 102 of flowchart 100. As stated above, system 36 comprises two tracking sub-systems: EM tracker sub-system 115 using sensors such as sensor 22, and ACL tracker sub-system 117 using currents through patches 60P. Each sub-system operates in a respective frame of reference. The EM tracker sub-system operates in an EM frame of reference that is generally fixed with respect to pad 43. The ACL tracker sub-system operates in an ACL frame of reference, the body coordinate system (BCS), that is assumed to be generally fixed with respect to patches 80R. Patches 80R enable measurements made in one of the sub-systems to be converted to the other sub-system. During the calibration phase reference patches 80R are attached to the back of subject 40, so that any motion of the subject with respect to pad 43 is reflected in signal changes in the EM sensors of the reference patches.

In the calibration phase processor 46 analyzes signals from the EM sensors on reference patches 80R, to determine an initial frame of reference for the BCS. During the tracking phase the processor analyzes signals from the EM sensors periodically, to determine changes in the location and orientation of the BCS frame of reference. The processor is able to detect if system parameters have changed beyond those expected, and in this event may return to the calibration phase.

In the calibration phase, the processor accumulates the location of patches 80R in LP coordinates, i.e., coordinates measured relative to location pad (LP) 43, for a time patchInitTime, typically approximately 1 sec.

The processor then calculates the mean location and the standard deviation for each patch:

$$\vec{\bar{P1}} = \frac{1}{N}\sum_i^N \vec{P1}_i \qquad (1)$$

$$\vec{P1}_{STD} = \sqrt{\sum_i^N \frac{1}{N}\left(\vec{P1}_i - \vec{\bar{P1}}\right)^2},$$

where i is a sample index,

N is the number of samples in time patchInitTime $\vec{P}1_i$ is a sample value, $\vec{P}1$ is the mean value of $\vec{P}1_i$ for each patch 1, and $\vec{P}1_{STD}$ is the standard deviation of $\vec{P}1$.

Providing the value of each $\vec{P}1_{STD}$ is less than a preset figure, typically approximately 1 mm, the calibration is accepted, in which case the mean $\vec{P}$ of all the means is set as the origin the BCS:

$$\vec{\tilde{P}} = \frac{1}{3}\sum_1^3 \vec{\tilde{P}1} \quad (2)$$

The radius vector from each patch to the origin is also calculated and saved for further use:

$$\vec{P}l\text{init}=\vec{\tilde{P}}l-\vec{\tilde{P}} \quad (3)$$

The mean vector defined by equation (2) and the three vectors defined by equation (3) are illustrated in FIG. 3. In addition to the origin, as defined by equation (2), the three vectors of equation (3) define a triangle in a plane, shown in the figure by broken lines between patches 80, 82, and 84. The initial BCS x, y, and z axes are defined using the triangle.

During the tracking phase of system 36, patches 80R may move, as exemplified by patches 80', 82', and 84', and processor 46 measures the new positions of the patches periodically, typically with a period of the order of one second. Embodiments of the present invention assume that the axes defined in the calibration phase move as an approximately rigid body, and processor 46 determines the translation and rotation of the axes from the new patch 80R positions during the tracking phase. Prior to the determinations, the new patch positions are filtered to reduce noise, the filtering typically comprising a low pass filter of the type:

$$y_i=ay_{i-1}+(1-a)x_i, \quad (4)$$

where $y_i$, $y_{i-1}$ are current and previous position estimates, $x_i$ is the current position measurement, and a is a factor between 0 and 1.

Typically "a" in equation (4) is selected so that there is an effective time constant of approximately 0.5 s in determining current position estimates $\vec{P}1$. Consequently, since body motion is usually slow, such a time constant does not significantly affect performance of system 36.

The filtered positions $\vec{P}1$ are used to determine a new origin vector of coordinates $\vec{P}_0$, substantially as described above for equation (3).

From the filtered positions $\vec{P}1$ processor 46 also determines a rotation matrix T, by methods which will be apparent to those having ordinary skill in the art, relating a new orientation of the axes with the original axes orientation. The processor then applies equation (5) (below) to transform each catheter tip location measurement back to the original BCS axes.

$$\vec{p}b=T^T\cdot(\vec{p}-\vec{P}_o) \quad (5)$$

where $T^T$ is the transpose of T, $\vec{p}$ is a vector representing a measured catheter tip location, and $\vec{p}b$ is a vector of the catheter tip relative to the original BCS axes.

The vector $\vec{p}$ is calculated in ACL step 114, described below.

Ablator Patch Compensation

As stated above with reference to FIG. 1A, control unit 44 comprises ablator 48 which is connected to the body of subject 40 by ablation patch 90 and ablation catheter 23. The ablation patch and the ablation catheter provide current paths to the ACL electrodes of catheters and/or 27, and to ACL patches 60P. In step 104 of flowchart 100 (FIG. 2), using ablator patch compensation module 119B, processor 46 compensates for currents being diverted to these paths, as described below.

Figure 4:
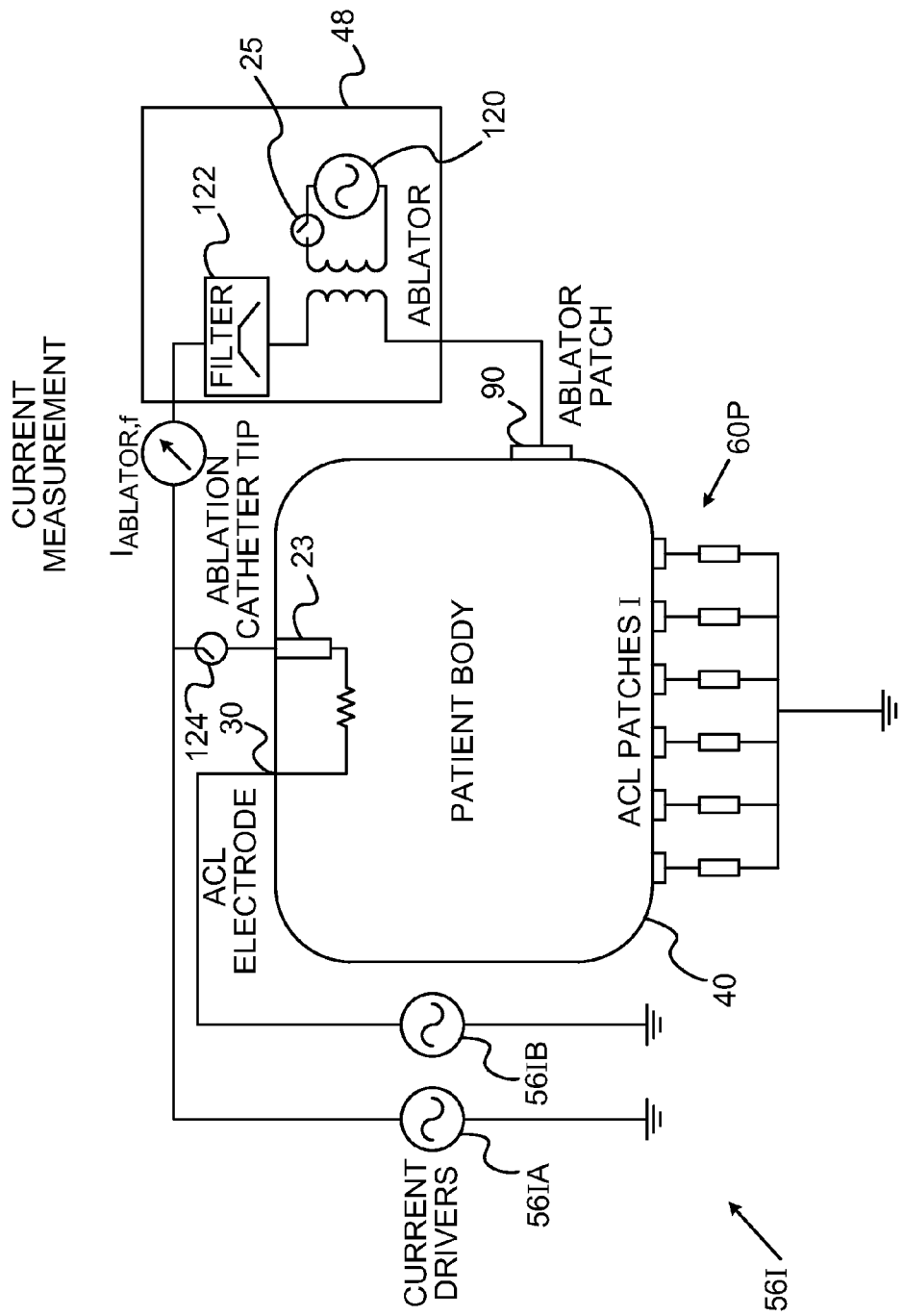
FIG. 4 is a schematic equivalent circuit diagram illustrating an ablator connected to a patient body, according to an embodiment of the present invention.

FIG. 4 is a schematic equivalent circuit diagram illustrating ablator 48 connected to patient body 40, according to an embodiment of the present invention. Current drivers 561 comprise a driver 561A which may inject current into ablation catheter tip 23, at a frequency $f_A$. Drivers 561 also comprise a driver 561B with which, in the tracking phase, system 36 may inject current into one of the ACL electrodes, herein assumed to be electrode 30, at a frequency $f_B$. Typically, there is a separate current driver with a respective separate frequency for each ACL electrode, but for simplicity only one such driver and electrode is shown in the figure. Both current drivers 561A and 561B may be controlled independently by processor 46. As is described in more detail below, the ACL electrode is tracked by analyzing the different currents in ACL patches 60P due to the current generated by driver 561B.

Ablator 48 comprises a radio-frequency (RF) generator 120 which is operated by professional 56 via switch 25, so as to perform a required ablation. Ablator 48 is connected to ablator patch 90, and is also connected via a band-pass filter 122 to the electrode of the tip of ablation catheter 23. Filter 122 acts as a low impedance for the RF energy from generator 120, and although it attenuates other frequencies, there is a current path for these frequencies which exists even if switch 25 is open. As is apparent from FIG. 4, there may be current paths other than the paths between an ACL electrode and ACL patches 60P. System 36 provides compensation for these paths, as explained below.

In the calibration phase, processor 46 opens a switch 124 to the ablation catheter tip, so that no current path exists via ablation catheter tip 23. In this state all current from driver 561A flows through ablator 48, via ablation patch 90, to ACL patches 60P.

Processor 46 operates current driver 561A at a single frequency $f_M$, which is typically close to 105 kHz. At frequency $f_m$ the processor measures the total current $\tilde{I}_{f_M}$ delivered by driver 561A, and the current through each ACL patch 60P, $I_{i,f_M}$ where i is an index for the patch. For all indices i, processor 46 calculates a set of ratios for the frequency $f_m$:

$$\{\alpha_{i,f_M}\} = \frac{I_{i,f_M}}{\tilde{I}_{f_M}} \quad (6)$$

The frequency dependency of the patches is known from calibration during manufacturing. Processor 46 uses the calibration to determine sets of ratios $\{\alpha_{i,f_A}\}$ for every operating frequency $f_A$ in a range including $f_M$. Typically if $f_m$ is 105 kHz, the range of $f_A$ is from approximately 100 kHz to approximately 110 kHz.

During the tracking phase and except when ablator 120 is operated by closure of switch 25, processor 46 may measure a leakage current $I_{ablator,f}$ through ablator patch 90 at each of the different general frequencies f which processor 46 uses for the catheters operating in system 36. The different measurements are typically made by performing a fast Fourier transform (FFT) on the measured current through the patch. In an embodiment wherein the leakage current is not measurable during operation of ablator 120, processor 46 may use the most recent measured leakage current before ablation starts as an estimate of the leakage current during ablation.

Alternatively, by using appropriate filters, and/or other hardware that will be apparent to those having ordinary skill in the art, processor 46 may measure leakage currents $I_{ablator,f}$ even when ablator 120 is being operated.

Also in the tracking phase, processor 46 measures currents $I_{i,f}$ through each of the ACL patches "i". The processor calculates an estimated current $\hat{I}_{i,f}$ at each frequency f to compensate for leakage through patch 90 according to equation (7):

$$\hat{I}_{i,f} = I_{i,f} - \hat{\alpha}_i(f) \cdot I_{ablator,f} \quad (7)$$

The estimated current $\hat{I}_{i,f}$ is used in patch calibration step 106, described below.

Patch Current Calibration

Ideally the impedance of each ACL patch measured to ground is zero, but this may not be the case in practice. If the impedances are different from zero, the measured currents through the patches may lead to errors in the predicted location of a catheter such as catheter 20, so that to reduce such errors, processor 46 uses a patch current calibration module 119C to perform a calibration on the ACL patches in patch calibration step 106 (FIGS. 2A and 2B). The calibration compensates for the impedances being non-zero, and also for differences in the impedances between the patches. The calibration enables processor 46 to estimate the current that would flow in a patch if the patch impedance is zero.

Figure 5:
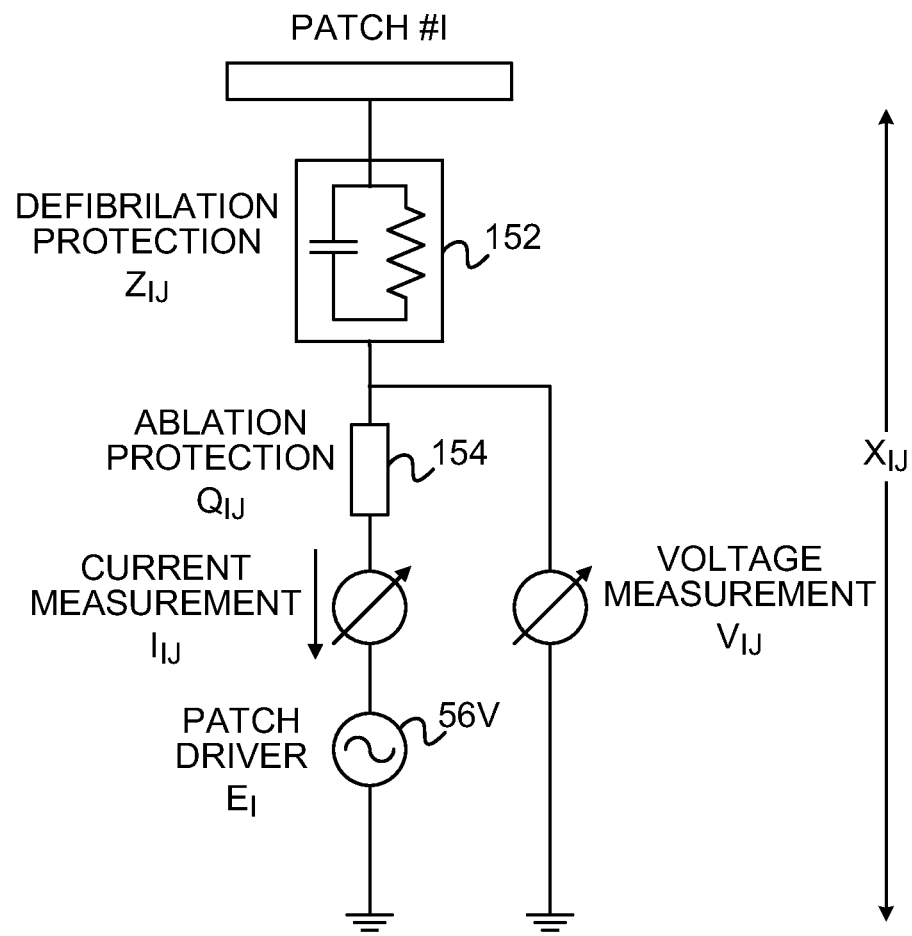
FIG. 5 is a schematic illustration of an active current location (ACL) patch circuit, according to an embodiment of the present invention.

Reference is now made to FIG. 5, which is a schematic illustration of an ACL patch circuit, according to an embodiment of the present invention.

All ACL patches have generally similar circuits. Each ACL patch i comprises a defibrillation protection circuit 152 and an ablation protection circuit 154. The two circuits are connected in series between the patch and ground. In FIG. 5, and for the analysis below, for each patch i, j is a frequency index, denoting the frequency $f_j$ transmitted by the patch.

$z_{ij}$ is a known impedance of defibrillation protection circuit 152. The known impedance may typically be provided by a patch box manufacturer, or determined from analysis of circuit 152.

$q_{ij}$ is the impedance of ablation protection circuit 154. The ablation protection circuit impedance is estimated during a patch impedance calibration process, described below.

$E_i$ is a voltage, from a voltage source 56V, that drives patch i with frequency $f_i$.

$I_{ij}$ is a current measured through patch i at frequency $f_i$.

$V_{ij}$ is a voltage measured on patch i at frequency $f_j$.

$X_{ij}$ is the actual voltage on patch i at frequency $f_j$.

In a patch impedance calibration procedure for system 36, processor 46 uses a respective voltage source 56V to inject current into each patch i at a corresponding frequencies $f_i$. The injected currents are also used in a patch effective area compensation procedure, described below.

The processor applies the two procedures referenced above, i.e., the patch impedance calibration procedure, and the patch effective area compensation procedure, in the calibration phase described above. The processor may also apply the two procedures in the tracking phase. For example, if the processor finds that the impedance $q_{ij}$ of the patch cannot be estimated, the patch impedance calibration procedure may be performed in the tracking phase.

The currents are injected at different frequencies j, and console 52 comprises ADCs (analog-to-digital circuits) which processor 46 multiplexes to measure values of $V_{ij}$ sequentially and values of $I_{ij}$ hsimultaneously.

In the patch impedance calibration procedure the processor estimates a value of $q_{ij}$ from the values of $V_{ij}$ and $I_{ij}$, typically by finding the ratio $$\frac{V_i}{I_i}$$

at each frequency j, and finding a best fit, typically a best quadratic fit, across the measured frequencies. Thus:

$$q_{ij} = \hat{q}_i(f_j) = \left[\frac{\overline{V}_{ij}}{\overline{I}_{ij}}\right] \quad (8)$$

During the tracking phase, processor 46 measures the values of $I_{ij}$ and $$\sum_i v_{ij}$$

at the different operating frequencies f. In the following analysis, the expressions of equation (9) are assumed.

$$\tilde{V}_j \equiv \sum_i V_{ij}, \quad (9)$$

and $$E_{ij} \equiv \delta_{ij} E_j$$

where $\tilde{V}_j$ is the sum of voltages measured on all patches at a frequency $f_j$, and $\delta_{ij}$ is the Kronecker delta.

For a particular patch i being driven at a frequency j, applying Ohm's law to ablation protection circuit 154 gives:

$$V_{ij} = E_{ij} + q_{ij} I_{ij},$$

so that $$\tilde{V}_j \equiv \sum_i V_{ij} = \sum_i (E_{ij} + q_{ij} I_{ij}) = \sum_i (\delta_{ij} E_j + q_{ij} I_{ij}) = E_j + \sum_i q_{ij} I_{ij}$$

which rearranged gives:

$$E_j = \tilde{V}_j - \sum_i q_{ij} I_{ij} \qquad (10)$$

Applying Ohm's law and equation (10) to the complete circuit of FIG. 5 gives, for a particular patch i:

$$\begin{aligned}X_{ij} &= E_{ij} + (q_{ij} + z_{ij})I_{ij} \\ &= \delta_{ij} E_j + (q_{ij} + z_{ij})I_{ij} \\ &= \delta_{ij}\left(\tilde{V}_j - \sum_k q_{kj} I_{kj}\right) + (q_{ij} + z_{ij})I_{ij}\end{aligned} \qquad (11)$$

where $X_{ij}$ is the overall voltage on patch i at frequency j.

The values of equation (11) may be used to determine a body conductance matrix σ, where σ is defined by the matrix equations:

$$-I = \sigma \cdot X, \text{ or } \sigma = -I \cdot X^{-1} \qquad (12)$$

where I is a matrix of patch currents, and X is a matrix of patch voltages. The patch currents may also be written as a vector s. The negative sign in equation (12) assumes a convention that positive current flows into body 40, and positive currents are also measured flowing out of the body. Alternatively, an equation similar to equation (12), using an impedance matrix Im, may be written relating matrices I and X.

Those having ordinary skill in the art will understand that a system conductance matrix σ', which is a combination of the body conductance matrix σ and a patch resistance matrix $R_k$, is given by:

$$\sigma' = (Id + \sigma \cdot R_k)^{-1} \cdot \sigma \qquad (13a)$$

where
Id is the identity matrix
σ is the conductance matrix defined in equation (12), and
$R_k$ is a diagonal matrix of patch resistances, with $(z_{ik} + q_{ik})$ as the $i^{th}$ diagonal element, for a catheter transmitting a frequency $f_k$.

If a voltage V is applied to the system, the current flowing in the system is given by:

$$\tilde{s} = \sigma' \cdot V = (Id + \sigma \cdot R_k)^{-1} \cdot \sigma \cdot V \qquad (13b)$$

where V is a voltage vector, and
$\tilde{s}$ is the measured current vector at frequency $f_k$.

Equation (13b) shows that $\tilde{s}$ is affected by the patch resistances. A calibrated current, that does not depend on the patch resistances and thus does not depend on frequency $f_k$, may be defined as:

$$s = \sigma \cdot V = (Id + \sigma \cdot R_k) \cdot \tilde{s} \qquad (13c)$$

where s is a calibrated current vector.

Processor 46 passes the estimated current values in each patch given by vector s to a patch effective area compensation process, described below.

Patch Effective Area Compensation

The description in this section explains patch compensation step 108 (FIG. 2A), wherein in patch effective area module 119F processor 46 performs a patch effective area compensation process that compensates for changes in the effective area of ACL patches i. In this section, patches 60P are differentiated by being referred to as patch i and patch j.

Some causes of changes to the effective area of the ACL patches are partial peeling of a patch from patient body 40, and skin conductivity changes, typically due to sweating. A patch effective area compensation model assumes that $$R_{ij} = G \cdot C_i \cdot C_j \cdot d_{ij} \qquad (14)$$

where
$R_{ij}$ is the impedance between patch i and patch j,
$C_i$, $C_j$ are effective areas of patch i and patch j
$d_{ij}$ is the distance between patches i and j, and
G is a constant of proportionality which is a function of, inter alia, medium conductivity.

In implementing the area compensation process, processor 46 generates a current $I_j$ from source patch j, and measures each of the currents $I_{ij}$ received in the other patches. Processor 46 performs the process for each ACL patch, so that for N patches, the processor makes a total of N(N−1) current measurements.

An estimated impedance $m_{ij}$ between any two patches i, j, is given by:

$$m_{ij} = \frac{V_j}{I_{ij}} \qquad (15)$$

where $V_j$ is the voltage driving patch j.

From equation (15) a normalized estimated impedance $\hat{m}_{ij}$ is given by:

$$\hat{m}_{ij} = \frac{m_{ij}}{\sum\limits_{\substack{k=1,\\k \neq j}}^{k=N} m_{kj}} = \frac{V_j / I_{ij}}{\sum\limits_{\substack{k=1,\\k \neq j}}^{k=N} V_j / I_{ij}} = \frac{1/I_{ij}}{\sum\limits_{\substack{k=1,\\k \neq j}}^{k=N} 1/I_{kj}} \qquad (16)$$

Processor 46 calculates and stores the values of $\hat{m}_{ij}$, using equation (16), during implementation of the area compensation process.

The current $I_j$ generated at patch j divides between the other patches in inverse proportion to the impedance between patch j and the other patches. Thus, the current $I_{ij}$ from source patch j to receiving patch i is given by:

$$I_{ij} = I_j \frac{1/R_{ij}}{\sum\limits_{k, k \neq j} 1/R_{kj}} \qquad (17)$$

Substituting equation (14) into equation (17) gives:

$$I_{ij} = \frac{I_j}{G C_i C_j d_{ij} \sum\limits_{k, k \neq j} 1/(G C_k C_j d_{kj})} = \frac{I_j}{C_i d_{ij} \sum\limits_{k, k \neq j} 1/(C_k d_{kj})} \qquad (18)$$

Substituting the value for $I_{ij}$ into equation (16), and simplifying, gives:

$$\hat{m}_{ij} = \frac{C_i d_{ij}}{\sum\limits_{n, n \neq j} C_n d_{nj}} \qquad (19)$$

where n is an integer from 1 to N, and N is the number of ACL patches.

Equation (19) may be written:

$$\sum_{n, n \neq j} (\hat{m}_{ij} - \delta_{ij}) C_n d_{nj} = 0 \quad (20)$$

As described above, processor 46 has determined the values of the relative impedances $\hat{m}_{ij}$.

In equation (20), inter-patch distances $d_{ij}$ may be measured using their respective associated tracking coils (and, when i=j, $d_{ij}$=0).

Equation (20) is a system of N(N−1) equations with N unknowns, i.e., the values $C_1, C_2, \ldots, C_N$. The system of equations (20) may be used to find the relative values of $C_i$. The system of equations is of the type $A \cdot \vec{C}=0$ wherein A is an N(N−1)×N matrix that depends on $\hat{m}_{ij}$ and $d_{ij}$, and wherein $\vec{C}$ is a vector representing the N values of $C_i$. Singular value decomposition (SVD) analysis of A or eigenvector analysis of the N×N matrix $A^T A$ provides a solution for $\vec{C}$, as is known in the art.

Assuming that processor 46 performs eigenvector analysis of the matrix $A^T A$, the processor selects the eigenvector with the smallest eigenvalue. Typically, the values of $\hat{m}_{ij}$ and $d_{ij}$ for matrices A and $A^T$ are filtered with a filter similar to equation (4), where the filter is adjusted to have a time constant of the order of 10 seconds. The smallest eigenvector corresponds to normalized values of the 6 areas $C_i$, herein termed $Ea_i$. Typically, processor 46 calculates the values of $Ea_i$ periodically, with a period that may be set by operator 56. In one embodiment, the period is of the order of 1 second.

The estimated current vector s, derived from equation (13c), gives 6 respective values of the currents $I_i$ in the ACL patches. To compensate for the patches effective area, $Ea_i$, processor 46 forms a normalized value of each of the currents:

$$In_i = \frac{I_i \cdot Ea_i}{\sum_{i=1}^{i=6} I_i \cdot Ea_i} \equiv (In6) \quad (21)$$

where (In6) is a six-dimensional current vector.

The normalization removes effects caused by changes in effective resistance in the region of the catheter electrode, such as may be caused by the electrode coming into contact with tissue, inhomogeneity of material surrounding the electrode, and/or instability of the source injecting current into the catheter electrode.

Current Projection

The 6 currents given by equation (21) have only five degrees of freedom since their sum is always one. To prevent singularities in further analysis of the currents, in current projection step 110 the 6 currents are converted, using a projection matrix J, to five independent quantities in current projection module 119D. Projection matrix J is derived by orthogonalization of a matrix, $$\begin{pmatrix} 1 & 1 & 1 & 1 & 1 & 1 \\ 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{pmatrix},$$

taking only the last five row vectors of the resulting matrix.

After orthogonalization, the last five rows of the orthogonalized matrix give:

$$J = \begin{pmatrix} -\frac{1}{\sqrt{30}} & \sqrt{\frac{5}{6}} & -\frac{1}{\sqrt{30}} & -\frac{1}{\sqrt{30}} & -\frac{1}{\sqrt{30}} & -\frac{1}{\sqrt{30}} \\ -\frac{1}{2\sqrt{5}} & 0 & \frac{2}{\sqrt{5}} & -\frac{1}{2\sqrt{5}} & -\frac{1}{2\sqrt{5}} & -\frac{1}{2\sqrt{5}} \\ -\frac{1}{2\sqrt{3}} & 0 & 0 & \frac{\sqrt{3}}{2} & -\frac{1}{2\sqrt{3}} & -\frac{1}{2\sqrt{3}} \\ -\frac{1}{\sqrt{6}} & 0 & 0 & 0 & \sqrt{\frac{2}{3}} & -\frac{1}{\sqrt{6}} \\ -\frac{1}{\sqrt{2}} & 0 & 0 & 0 & 0 & \frac{1}{\sqrt{2}} \end{pmatrix} \quad (22)$$

The currents from equation (21) are thus projected to five current-equivalents according to equation (23):

$$(In5) = J \cdot (In6) \quad (23)$$

In addition to performing the normalization of equation (23), in current projection step 110 processor also normalizes respiration indicators. The respiration indicators are measures of changes in resistance between ACL patches caused by the respiration of the patient, and the processor uses the indicators to extract, in step 112, the frequency band corresponding to the frequency of respiration. The respiration indicators are generally similar in properties to the patch effective areas $(C_i)$, and an expression for the indicators is derived using equation (20). From equation (20), $$C_i = \frac{\hat{m}_{ij}}{d_{ij}} \sum_n C_n d_{nj} \quad (i \neq j) \quad (24)$$

Averaging equation (24) over j, and assuming as an approximation that $d_{ij}=1 (i \neq j)$; $d_{ij}=0 (i=j)$, we define a respiration indicator $RI_i$ for patch i as:

$$RI_i = \sum_j \hat{m}_{ij} \sum_n RI_n d_{nj} = \sum_n RI_n \left( \sum_n \hat{m}_{ij} d_{nj} \right) \quad (25)$$

Assuming $RI_i$ is written as an N-dimensional vector $RIi$, $\widehat{m_{ij}}$ may be written as an N×N matrix M, with 0 at the diagonals, and $\widehat{d_{ij}}$ may be written as a matrix D, given by equation (26):

$$D = \begin{pmatrix} 0 & 1 & 1 & 1 & 1 & 1 \\ 1 & 0 & 1 & 1 & 1 & 1 \\ 1 & 1 & 0 & 1 & 1 & 1 \\ 1 & 1 & 1 & 0 & 1 & 1 \\ 1 & 1 & 1 & 1 & 0 & 1 \\ 1 & 1 & 1 & 1 & 1 & 0 \end{pmatrix} \quad (26)$$

In this case processor 46 iteratively estimates a new vector $RI_{i,t}$ from a previous estimate $RI_{i,t-1}$ and a new measurement $\widehat{m_{ij}}$ according to the two step process:

$$\overline{RI_{i,t}} = M^T \cdot D \cdot RI_{i,t-1}, \text{ then} \quad (27)$$

$$RI_{i,t} := \frac{\overline{RI_{i,t}}}{\sum_i \overline{RI_{i,t}}}$$

where t is a parameter indicating the sequential order of $RI_{i,t}$ and $RI_{i,t-1}$.

Vector $RI_{i,t}$ is six-dimensional, but has only five degrees of freedom (as in the currents of equation (21). As shown in equation (28) below, the values of $RI_i$ derived from equation (27) are further converted in the same manner as the currents of equation (21), by multiplying by matrix J, to give five patch respiration equivalents.

$$(RI_i 5) = J \cdot (RI_i 6) \quad (28)$$

Temporal Decomposition

Embodiments of the present invention may operate in substantially any region of the body of the patient, and all such regions exhibit at least some motion. The heart environment is particularly dynamic, and the motions of the heart affect the current measurements of the ACL patches. Significant mechanisms affecting the measurements are the heartbeat and respiration processes. A slower process that also may affect the current measurements is a drift of a reference catheter, typically a movement of CSRC 27 (FIG. 1A).

Reference is now made to FIG. 6, which is a graph of different components of the location of a CSRC, and to FIG. 7, which is a graph of a frequency response of a filter, according to an embodiment of the present invention. The graph in FIG. 6 illustrates temporal decomposition over the direction that maximizes the respiration effect on the CSRC location. The graph is for an animal case, but the decomposition is generally similar to that occurring in a human case. A line 230 represents a measured location (minus its mean), which is decomposed to three signals. A first signal line 232 represents mainly a heartbeat component, a second signal line 234 represents a respiration effect, and a third signal line 236 represents location drift.

In temporal adjustment step 112 (FIG. 2) the ACL current measurements from step 110, and location measurements from the EM detector in catheters having such detectors, are filtered to determine the drift, heartbeat, and respiration components illustrated in FIG. 6. In temporal decomposition module 119E processor 46 filters these components from the current and location measurements, and passes the filtered values for processing in the ACL tracker, described below. The unfiltered values, as well as the values that the filters have extracted, are also available to the ACL tracker.

The drift component is calculated by applying a very low pass filter, typically a filter having a time constant of the order of approximately 10 seconds. The low pass filter may be implemented using an equation of the form of equation (4). The drift component is herein referred to as $Ydr_i$.

The respiration component is calculated by applying a Finite Impulse Response (FIR) filter to the current and location measurements. The FIR filter acts as a low pass filter, and a frequency response of an appropriate filter is shown in FIG. 7. An FIR filter of the form given by equation (29) below may be used to generate the frequency response $$FIR(x_i, k) = \sum_j x_{i-j} \cdot k_j \quad (29)$$

where
k is a kernel having j values $k_j$,
$x_i$ are the current and location measurements, and
$FIR(x_i, k)$ are the filtered values.

The respiration component is the FIR output less the drift component, i.e., it is $FIR(x_i,k) - Ydr_i$.

In order to remove the heartbeat component from the measured location, a low pass filter with a 1 second window may be applied. This causes a process delay of about half a second between each location measurement and a corresponding temporal decomposition output. This results in a half-second delay between any movement of catheter 20 and a corresponding update to visual display 54 (FIG. 2).

All measurements made in the temporal decomposition step are passed to ACL tracker module 121, in ACL step 114 of flow chart 100 (FIGS. 2A and 2B).

ACL Tracker

In ACL step 114 ACL tracker module 121 calculates the location of catheters such as catheter 20 and catheter 21, using the temporally decomposed current measurements generated in step 112. The measurements generated in step 112 are combined into a current-to-position mapping (CPM) vector $\vec{m}$.

Figure 8:
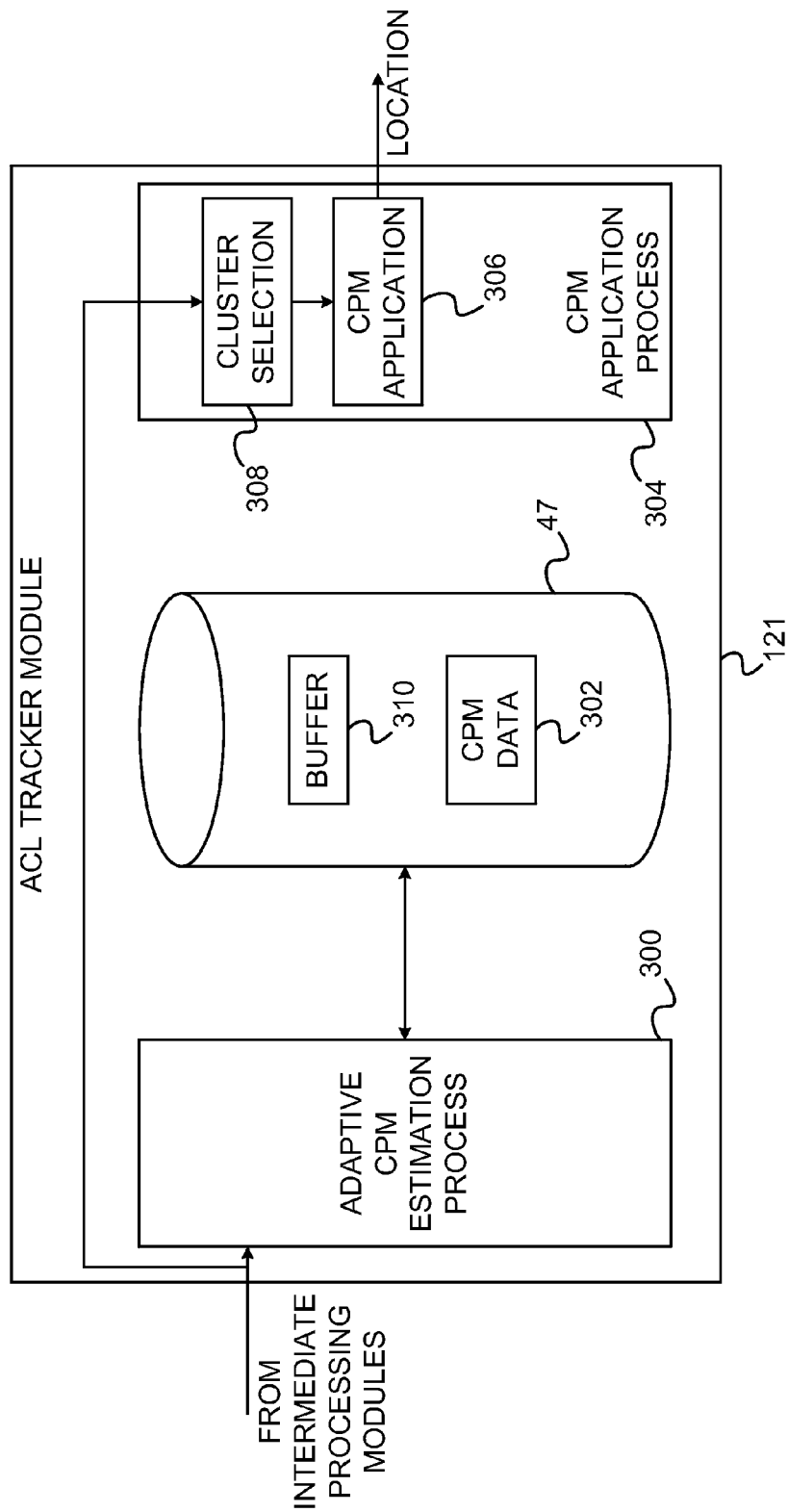
FIG. 8 is a simplified block diagram illustrating components of an ACL tracker module, according to an embodiment of the present invention.
Figure 9:
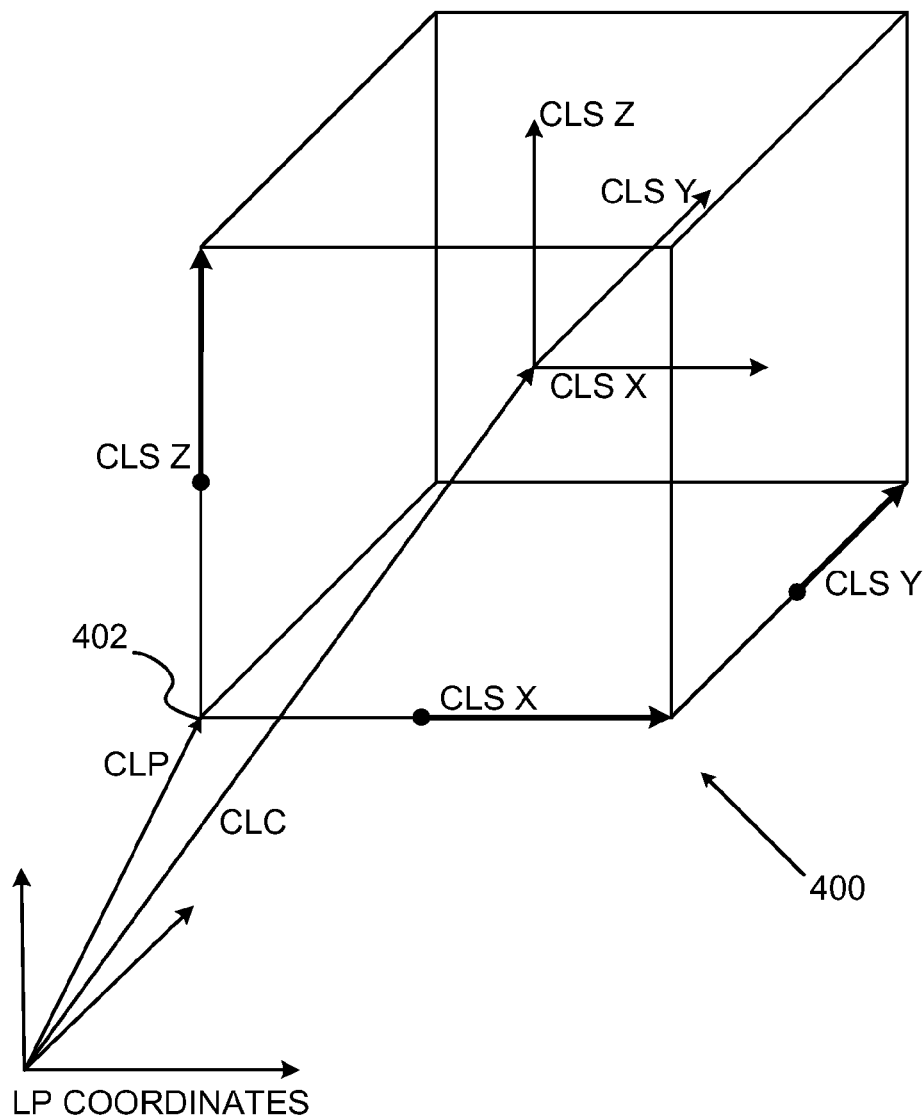
FIG. 9 is a diagram showing parameters used in defining sub-volumes into which a region being investigated is divided, according to an embodiment of the present invention.

FIG. 8 is a simplified block diagram illustrating components of the ACL tracker module, and FIG. 9 is a diagram showing parameters used in defining sub-volumes into which the region being investigated is divided, according to embodiments of the present invention.

The ACL tracker module comprises two components, an adaptive CPM estimation process 300 and a CPM application process 304. CPM application process 304 further comprises a cluster selection module 308, and a CPM application module 306, the functions of which are described below.

The adaptive CPM estimation process uses measurements from any hybrid catheter having an EM sensor and associated electrode, such as catheter 20, the measurements being included in vectors $\vec{m}$, to calculate CPM matrices. In embodiments of the present invention, a respective matrix is calculated for each sub-volume 400, also herein termed a cluster volume or a cluster, of the region being investigated. The region being investigated is divided into different sizes of clusters according to a resolution set for a particular cluster level. Thus, at a low resolution level the region may be divided into 16 clusters, each cluster having a matrix. At a higher resolution, the region may be divided into 1024 clusters having respective matrices.

The matrices constructed in the CPM estimation process take time to build, so that there is an initialization period for ACL step 114 during which period processor 46 receives initial data from decomposition step 112. For a particular cluster, once the processor has accumulated sufficient data for that cluster, the processor is able to generate a matrix for the cluster. The generated matrix is stored as CPM data 302 in memory 47 (FIG. 1A).

The CPM application uses the generated matrices, with current measurements for cathode electrodes, to calculate each electrode location in real-time. The calculation is performed according to the following equation:

$$\vec{p} = A \cdot \vec{m} \quad (30)$$

where $\vec{m}$ is the CPM vector built from the temporally decomposed current measurements, A is the matrix for a particular cluster, and $\vec{p}$ is the position vector of the electrode, also referred to in equation (5) above.

The CPM vector $\vec{m}$ typically has the following four sets of elements:

(i) 5 current elements, corresponding to the values derived from equation (23), for a mapping catheter, and (ii) 6 patch respiration indicators $\vec{Rs_i}$, corresponding to the $RI_i$ values derived from equation (28).

In addition to the above elements, if a reference catheter such as CSRC 27 is used, vector $\vec{m}$ may also comprise:

(iii) 5 reference catheter current elements, and (iv) 3 reference catheter location elements.

The elements in sets (ii), (iii), and (iv) are values derived after the temporal decomposition described above, i.e. minus the drift component for set (ii), and minus the respiration component in sets (iii) and (iv).

The processor uses the respiration indicators $\vec{Rs_i}$ to generate a respiration descriptor, which is a value indicating at which time a measurement is in the respiration cycle.

The respiration descriptor is typically generated initially, once a patient is positioned as shown in FIG. 1A, and after patches i have been attached. During a respiration training period, typically of the order of 30 sec, processor 46 accumulates values of the respiration indicators $\vec{Rs_i}$.

Once respiration indicators have been accumulated, the processor performs principal component analysis (PCA) on the indicators to find a direction between the elements having a largest eigenvalue as follows:

$$\vec{Rdir} = \\ EigenVector\left(\left[\vec{Rs_i} - Mean(\vec{Rs_i})\right] \cdot \left[\vec{Rs_i} - Mean(\vec{Rs_i})\right]^T\right)\bigg|_{Max \atop (eigen-value)} \quad (31)$$

The direction given by equation (31) is used to calculate a respiration descriptor value as follows:

$$RD_i = \vec{Rdir} \cdot \vec{Rs_i} \quad (32)$$

where $RD_i$ is the respiration descriptor for the $i^{th}$ patch.

The mean and range of the $RD_i$ values are calculated as follows:

$$RDmean = \frac{1}{N}\sum_{i=1}^{n} RD_i; \; \vec{RDrange} = \text{Max}(RD_i) - \text{Min}(RD_i) \quad (33)$$

The mean and range are used to calculate a normalized value $RDn_i$ of $RD_i$ that is in a range from 0 to a maximum value ClNo, as in equation (34) below. CLNo is a number defining a resolution of an update holder, described below, and is typically approximately 5.

$$RDn_i = \frac{RD_i - Rmean + \frac{Rrange}{2}}{\vec{Rrange}} ClNo \quad (34)$$

The values of $RDn_i$ are stored in memory 47.

FIG. 9 illustrates parameters used to define cluster volume 400. The parameters used are vectors measured in the EM tracker frame of reference (FIG. 3) Each cluster volume 400 is referenced by its left-rear-bottom corner 402, also herein termed the cluster origin, which is a vector $Clp_{RL}$ having the lowest values of x, y, and z for any point comprised in the cluster. Cluster volume 400 is defined by its center, Clc, rectilinear lengths Cls from the center, and a cluster resolution level vector $Clr_{RL}$, which defines lengths of the sides of clusters at a resolution level RL.

Measured in mms, typical default values of Clc and Cls and $Clr_{RL}$ are:
Clc=(0, 0, 280)
Cls=(150, 150, 200)
$Clr_{RL}$=(50, 20, 5), for a resolution level RL=1 (the coarsest resolution). For larger values of RL, corresponding to higher resolutions, the values of the coordinates of $Clr_{RL}$ decrease.

The default values of Cls and $Clr_{RL}$ correspond to a volume that is a box having dimensions of 300 mm×300 mm×400 mm. This volume is divided into equal-sized clusters having smaller dimensions. For the default values given above there are 6×15×80 clusters in the box.

For a given location $p_i$, a cluster index of an associated cluster is found by calculating the following expressions:

$$Cldim = 2\frac{Cls}{Clr_{RL}} + (1, 1, 1) \quad (35)$$

$$ClRng = (Cldim_y Cldim_z, Cldim_z, 1)$$

$$Clx_{i,RL} = \left\lfloor \frac{\vec{p_i} - Clc + Cls}{Clr_{RL}} \right\rfloor \cdot ClRng + 1$$

In expressions (35):
Cldim is a vector ($Cldim_x, Cldim_y, Cldim_z$), where the coordinates of the vector correspond to the number of clusters in each dimension;
Vector division is evaluated by dividing each element of the vector numerator by the corresponding element of the vector denominator, so that, for example, $$\frac{(20, 30, 40)}{(5, 6, 4)} = (4, 5, 10);$$

The vector multiplication in the last expression is a dot, or scalar, product.

Given a cluster index $Clx_{i,RL}$, the cluster origin is found by applying the following expressions recursively:

$$Clx_{i,RL} = Clx_{i,RL} - 1 \qquad (36)$$

$$\left(q_j = \left\lfloor \frac{Clx_{i,RL}}{ClRng_j} \right\rfloor, (Clinx = Clinx - q_j ClRng_j)\right), \{j = 1, 2, 3\}$$

$$\vec{C}lp_{RL} = qClr_{RL} + Clc - Cls$$

where Clinx has an initial value $Clx_{i,RL}$.

The update holder referred to above is an index that flags locations that have been used to update the cluster CPM matrix. The index prevents multiple measurements from a location being used to calculate the matrix. An update holder index (Uhl) is calculated as follows:

$$Uhl = \lfloor (ClNo(\vec{p} - \vec{C}lp_1)/Clr_1 + ClNo, RDn)\rfloor \cdot ((3ClNo)^3, (3ClNo)^2, ClNo, 1) + 1 \qquad (37)$$

Figure 10:
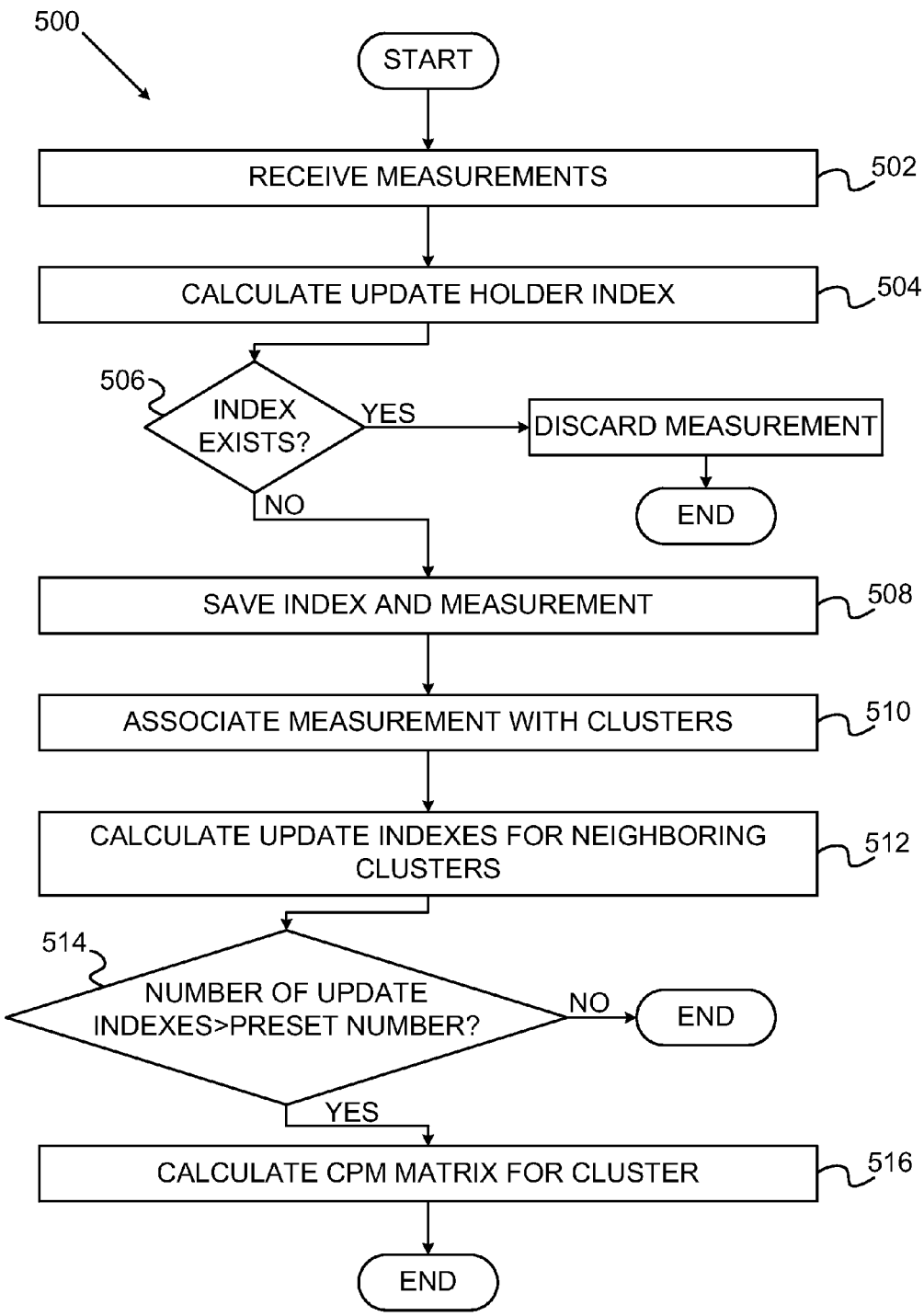
FIG. 10 is a flowchart showing steps taken by a processor in the position sensing system to generate current-to-position mapping (CPM) matrices, according to an embodiment of the present invention.

FIG. 10 is a flowchart 500 showing steps taken by processor 46 to generate CPM matrices, according to an embodiment of the present invention. The steps of the flowchart are performed in adaptive CPM estimation process 300 as each measurement is generated by catheter 20.

In an initial step 502, measurements are received from any hybrid catheter, and the processor forms the measurements into a CPM vector $\vec{m}$, as described above.

In a first update holder step 504, the update holder index for the measurement is calculated, using equation (37).

In a first condition 506, the processor checks to see if the update holder index already exists, by checking to see if the index has been saved in memory 47. If the index does exist, the measurement is discarded and the flowchart ends.

If the index does not exist, then in a save step 508 the index and the measurements are saved in a buffer 310 (FIG. 8) in memory 47. The measurements are saved as a vector $\vec{m}$.

In a cluster association step 510, the measurement is associated with corresponding clusters. The association is performed by calculating from the measurement the corresponding cluster index, according to equation (35). The measurement is associated with this cluster index.

The cluster origin, $\vec{C}lp_{RL}$, is then calculated, using equation (36). From this point, the cluster origins of all existing nearest neighbor clusters, up to 26 of which are possible in total, are found using equation (38):

$$\vec{C}lp_{RL,n} = \vec{C}lp_{RL} + d_n Clr_{RL}, n = 1 \ldots 26, \qquad (38)$$

where $d_n = \{\{-1,-1,-1\}, \{-1,-1,0\}, \{-1,-1,1\}, \{-1,0,-1\}, \{-1,0,0\}, \{-1,0,1\}, \{-1,1,-1\}, \{-1,1,0\}, \{-1,1,1\}, \{0,-1,-1\}, \{0,-1,0\}, \{0,-1,1\}, \{0,0,-1\}, \{0,0,1\}, \{0,1,-1\}, \{0,1,0\}, \{0,1,1\}, \{1,-1,-1\}, \{1,-1,0\}, \{1,-1,1\}, \{1,0,-1\}, \{1,0,0\}, \{1,0,1\}, \{1,1,-1\}, \{1,1,0\}, \{1,1,1\}\}$ From the values of $\vec{C}lp_{RL}$ the cluster indexes of all the nearest neighbor clusters are calculated from equation (35).

The calculations in this step are applied for all values of RL.

In a second update holder step 512, the update holder indexes for the neighboring clusters are calculated using the measurement received in step 502 and equation (37). If an update index is not already occupied, the measurement is placed in buffer 310, and the index is saved. If the index is already occupied, no action is taken.

In a second condition 514, the number M of update indexes in each cluster Clx is evaluated. If M is larger than a preset number, typically of the order of 40, then in a cluster matrix step 516 the CPM matrix A of the cluster is calculated, using equation (39):

$$A_{Clx,RL} = [\vec{m}_1; \vec{m}_2; \ldots \vec{m}_M]^{-1} \cdot [\vec{p}_1; \vec{p}_2; \ldots \vec{p}_M] \qquad (39)$$

where $\vec{p}_n$ is the measured location of the hybrid catheter, and $\vec{m}_n$ is the CPM vector, described above with reference to equation (30), for update index n, n=1, 2, ... M.

Typically, two CPM matrices A are calculated for each cluster, one using measurements with a reference catheter such as CSRC 27, one without the reference catheter measurements, and flowchart 500 then ends.

If in condition 514 M is not larger than the preset number, flowchart 500 ends.

Typically, the calculations in flowchart 500 are checked at various stages, to verify that the calculated results are self-consistent. For example, in cluster association step 510, if the number of existing neighboring clusters is less than a preset number, for example 4, an error may be assumed and the measurement of step 502 is not accepted. Other self-consistency checks for the operation of the flowchart will be apparent to those having ordinary skill in the art.

Figure 11:
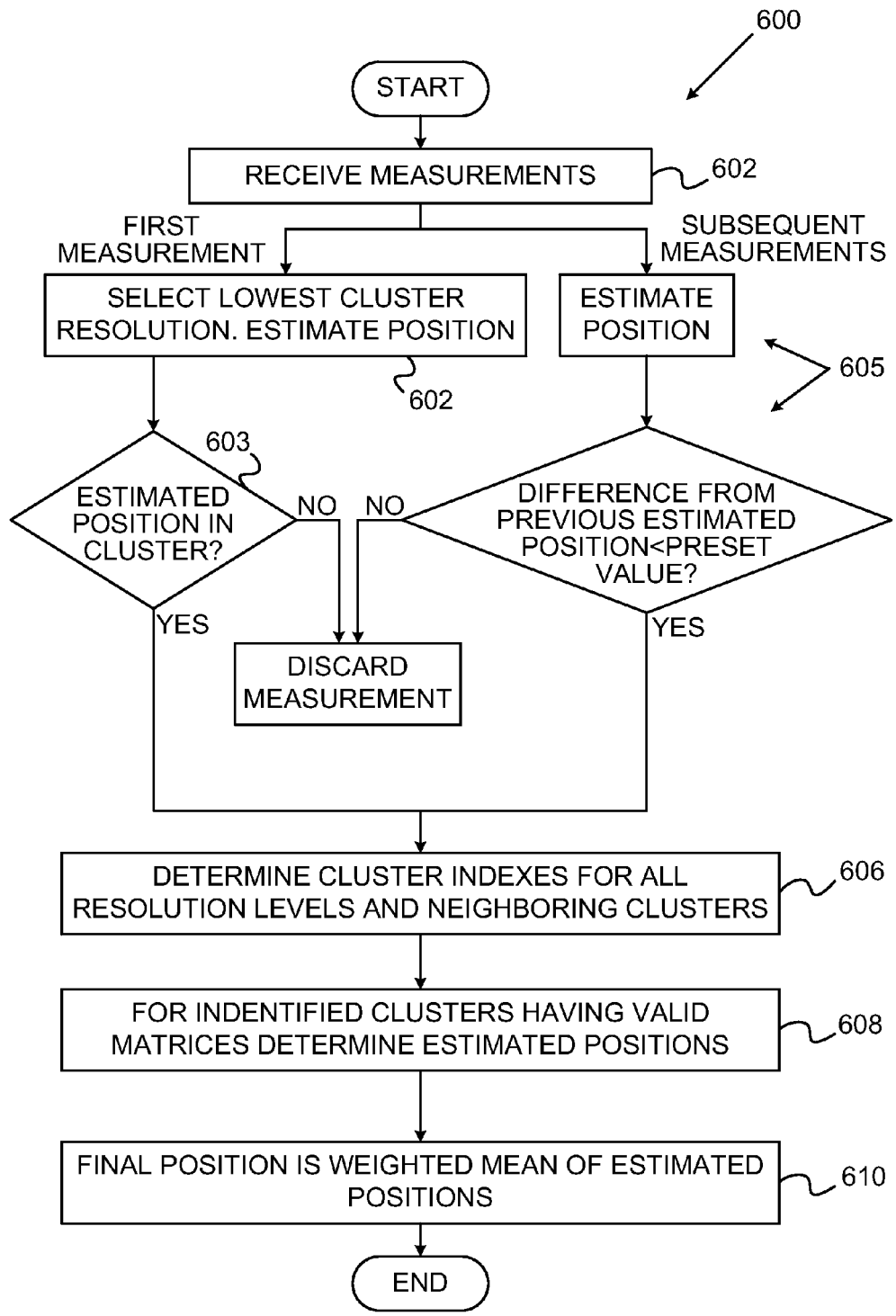
FIG. 11 is a flowchart showing steps taken by the processor to generate catheter positions using the CPM matrices generated in the flowchart of FIG. 10, according to an embodiment of the present invention.

FIG. 11 is a flowchart 600 showing steps taken by processor 46 to generate catheter positions using the CPM matrices generated in flowchart 500, according to an embodiment of the present invention. The flowchart uses the measurements that are also used to generate the CPM matrices.

An initial step 602 is generally similar to initial step 502 (FIG. 10), wherein measurements are received from a hybrid catheter, and the processor forms the measurements into a CPM vector $\vec{m}$.

If the measurement $\vec{m}_1$ is the first measurement from the catheter, then in a position calculation step 604, in cluster selection module 308 the lowest cluster resolution, RL=1, is selected. An estimate $\hat{\vec{p}}_1$ of the position is made according to equation (40):

$$\hat{\vec{p}}_1 = \text{Min}(\vec{m}_1 \cdot A_{Clx,1} - \vec{C}lp_1(Clx)); Clx = 1 \ldots M \qquad (40)$$

where Clx is a cluster index for CPM matrices $A_{Clx,l}$, that is assumed to vary from 1 to M; and $\vec{C}lp_1(Clx)$ is the cluster origin of the cluster with index Clx, calculated according to equation (35).

In a first condition 603 the value from equation (40) is checked to ensure it is within the cluster volume (with cluster index Clx), by verifying that:

$$\|\hat{\vec{p}}_1 - \vec{C}lp_1(Clx)\| < \sqrt{3} Clr_1 \qquad (41)$$

Equations (40) and (41) are applied to incoming measurements until expression (41) is valid, producing a first valid position estimation $\hat{\vec{p}}_1$.

For subsequent measurements $\vec{m}_i$, i.e., in subsequent measurement steps 605, the validity of the determined position is checked by evaluating the difference between the immediately preceding position estimates, and verifying that the difference does not exceed a preset value. If the difference is exceeded, the measurement is discarded.

In a resolution level step 606, the cluster indexes for all resolution levels RL are calculated, using equation (35). In addition, the neighboring cluster indexes n are identified, using the process described above with respect to equation (38).

In a multiple location step 608, CPM matrices A that are valid, for the clusters identified in step 606, are used to determine estimated positions $\hat{\vec{p}}_{i,RL,n}$ for measurement $\vec{m}_i$, according to equation (42):

$$\hat{\vec{p}}_{i,RL,n} = \vec{m}_i \cdot A_{RL,n} \qquad (42)$$

In a final location estimation step 610, the values determined in equation (42) are weighted, using a Gaussian weighting factor:

$$w_{RL,n} = \frac{1}{\sqrt{2\pi}\, C1r_{RL}} e^{-\frac{(\vec{C1}p_{RL,n} - \hat{\vec{p}}_{i-1})^2}{C1r_{RL}^2}} \qquad (43)$$

Processor 46 uses the weighting factor to form a final weighted sum of all clusters at all levels, generating a final estimated location, according to equation (44):

$$\hat{\vec{fp}}_i = \frac{\sum_{RL,n} w_{RL,n} \cdot \hat{\vec{p}}_{i,RL,n}}{\sum_{RL,n} w_{RL,n}} \qquad (44)$$

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for position tracking, comprising:
    an investigation-tool having a conductive-electrode which is coupled to generate currents in a body of a patient in response to a driving voltage applied to the conductive-electrode:
    an ablator body electrode, positioned in galvanic contact with the body, and configured to transfer ablation current to the body;
    body surface electrodes, positioned in galvanic contact with the body, which receive respective body surface currents from the conductive-electrode; and
    a processor which determines a location of the investigation-tool in response to the respective body surface currents, while compensating for diversion of the respective body surface currents by the ablator body electrode.

2. The apparatus according to claim 1, wherein compensating for the diversion comprises recording the respective body surface currents prior to the transfer of the ablation current, and determining the location using the recorded respective body surface currents.

3. The apparatus according to claim 1, wherein compensating for the diversion comprises applying an ablator-body-electrode driving voltage to the ablator body electrode, and determining calibration currents in the body surface electrodes formed in response to the ablator-body-electrode driving voltage.

4. The apparatus according to claim 3, and comprising an ablator configured to generate the ablation current, and wherein applying the ablator-body-electrode driving voltage to the ablator body electrode comprises applying the ablator-body-electrode driving voltage via the ablator.

5. The apparatus according to claim 3, and comprising an ablator catheter, and wherein applying the ablator-body-electrode driving voltage comprises applying the ablator-body-electrode driving voltage while decoupling the ablator catheter from the ablator.

6. The apparatus according to claim 3, and comprising an ablator catheter, and wherein applying the ablator-body-electrode driving voltage comprises applying the ablator-body-electrode driving voltage while the ablator catheter is coupled to the ablator.

7. A method for estimating impedance, comprising:
    positioning body-electrodes in galvanic contact with a body of a patient;
    positioning an investigation-tool having a conductive electrode in a plurality of regions within the body;
    for each region, generating respective inter-electrode currents between the body-electrodes;
    for each region, generating respective investigation-tool currents between the conductive electrode and the body-electrodes; and
    for each region, determining a respective impedance between each of the body-electrodes and the body in response to the respective inter-electrode currents and the respective investigation-tool currents.

8. The method according to claim 7, wherein generating the respective inter-electrode currents comprises setting the inter-electrode currents to be respective alternating currents having different respective frequencies.

9. A method for position tracking, comprising:
    coupling an investigation-tool having a conductive-electrode to generate currents in a body of a patient in response to a driving voltage applied to the conductive-electrode:
    positioning an ablator body electrode in galvanic contact with the body so as to transfer ablation current to the body;
    positioning body surface electrodes in galvanic contact with the body so to receive respective body surface currents from the conductive-electrode; and
    determining a location of the investigation-tool in response to the respective body surface currents, while compensating for diversion of the respective body surface currents by the ablator body electrode.

10. The method according to claim 9, wherein compensating for the diversion comprises recording the respective body surface currents prior to the transfer of the ablation current, and determining the location using the recorded respective body surface currents.

11. The method according to claim 9, wherein compensating for the diversion comprises applying an ablator-body-electrode driving voltage to the ablator body electrode, and determining calibration currents in the body surface electrodes formed in response to the ablator-body-electrode driving voltage.

12. The method according to claim 11, and comprising configuring an ablator to generate the ablation current, and wherein applying the ablator-body-electrode driving voltage to the ablator body electrode comprises applying the ablator-body-electrode driving voltage via the ablator.

13. The method according to claim 11, and comprising providing an ablator catheter, and wherein applying the ablator-body-electrode driving voltage comprises applying the ablator-body-electrode driving voltage while decoupling the ablator catheter from the ablator.

14. The method according to claim 11, and comprising providing an ablator catheter, and wherein applying the ablator-body-electrode driving voltage comprises applying the ablator-body-electrode driving voltage while the ablator catheter is coupled to the ablator.

15. Apparatus for estimating impedance, comprising:
body-electrodes positioned in galvanic contact with a body of a patient;
an investigation-tool having a conductive electrode, configured to be positioned in a plurality of regions within the body; and
a processor, which for each region is configured to:
generate respective inter-electrode currents between the body-electrodes,
generate respective investigation-tool currents between the conductive electrode and the body-electrodes, and
determine a respective impedance between each of the body-electrodes and the body in response to the respective inter-electrode currents and the respective investigation-tool currents.

16. The apparatus according to claim 15, wherein generating the respective inter-electrode currents comprises setting the inter-electrode currents to be respective alternating currents having different respective frequencies.

* * * * *